(12) United States Patent
Binderup et al.

(10) Patent No.: US 6,525,077 B2
(45) Date of Patent: Feb. 25, 2003

(54) CYANOGUANIDINE PRODRUGS

(75) Inventors: Ernst Binderup, Tåstrup (DK); Pernille-Julia Vig Hjarnaa, Espergærde (DK)

(73) Assignee: Leo Pharmaceutical Products Ltd. A/S, Ballerup (DK)

( * ) Notice: Subject to any disclaimer, the term of this patent is extended or adjusted under 35 U.S.C. 154(b) by 0 days.

(21) Appl. No.: 09/988,819

(22) Filed: Nov. 20, 2001

(65) Prior Publication Data

US 2002/0165201 A1 Nov. 7, 2002

Related U.S. Application Data

(60) Provisional application No. 60/252,078, filed on Nov. 21, 2000.

(51) Int. Cl.[7] .................. C07D 213/75; A61K 31/44
(52) U.S. Cl. ........................................ 514/353; 546/306
(58) Field of Search ........................... 546/306; 514/353

(56) References Cited

FOREIGN PATENT DOCUMENTS

| EP | 660823 (WO 94/06770) | 3/1994 |
|---|---|---|
| WO | WO 98/54141 | 12/1998 |
| WO | WO 98/54143 | 12/1998 |
| WO | WO 98/54144 | 12/1998 |
| WO | WO 98/54145 | 12/1998 |
| WO | WO 00/61559 | 10/2000 |
| WO | WO 00/61561 | 10/2000 |

*Primary Examiner*—Zinna Northington Davis
(74) *Attorney, Agent, or Firm*—Birch, Stewart, Kolasch & Birch, LLP

(57) ABSTRACT

A compound of the formula

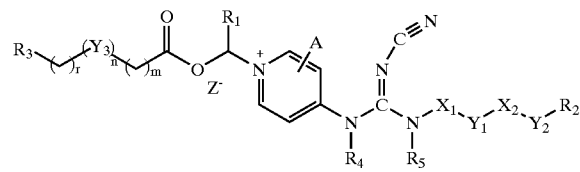

is disclosed, the compound being suited for therapeutical uses. The invention also discloses compositions comprising said compound, methods of treatment involving administering said compound to a patient, and the use of said compound in the manufacture of medicaments.

32 Claims, No Drawings

CYANOGUANIDINE PRODRUGS

This application claims the benefit of U.S. Provisional Application No. 60/252,078, filed Nov. 21, 2000.

FIELD OF INVENTION

The present invention relates to novel pyridyl cyanoguanidine prodrugs and their inclusion in pharmaceutical compositions, as well as their use in the manufacture of medicaments.

BACKGROUND OF THE INVENTION

Pyridyl cyanoguanidines such as pinacidil (N-1,2,2-trimethylpropyl-N'-cyano-N"-(4-pyridyl)guanidine) were originally discovered to be potassium channel openers and were consequently developed as antihypertensive agents. Replacement of the side chain of pinacidil by longer aryl-containing side chains caused a loss of the antihypertensive activity, but such compounds were, on the other hand, found to show antitumour activity on oral administration in a rat model carrying Yoshida ascites tumours.

Different classes of pyridyl cyanoguanidines with antiproliferative activity are disclosed in, for instance, EP 660 823, WO 98/54141, WO 98/54143, WO 98/54144, WO 98/54145, WO 00/61559 and WO 00/61561. The structure-activity relationships (SAR) of such compounds are discussed in C. Schou et al., *Bioorganic and Medicinal Chemistry Letters* 7(24), 1997, pp. 3095–3100, in which the antiproliferative effect of a number of pyridyl cyanoguanidines was tested in vitro on different human lung and breast cancer cell lines as well as on normal human fibroblasts. The compounds were also tested in vivo in nude mice carrying a human lung cancer tumour xenograft. Based on the SAR analysis, a specific compound (N-(6-(4-chlorophenoxy)hexyl)-N'-cyano-N"-(4-pyridyl)guanidine) was selected for its high antiproliferative activity in vitro and potent antitumour activity in the nude mouse model.

P-J V Hjarnaa et al., *Cancer Res.* 59, 1999, pp. 5751–5757, report on the results of further testing of the compound N-(6-(4-chlorophenoxy)hexyl)-N'-cyano-N"-(4-pyridyl)guanidine in in vitro and in vivo tests. The compound exhibited a potency in vitro which was comparable to that of the reference cytostatic agents daunorubicin and paclitaxel, while showing considerably less antiproliferative activity on normal human endothelial cells. In in vivo tests using nude mice transplanted with human tumour cells, the compound showed substantial antitumour activity, also against tumour cells that were resistant to conventional anticancer drugs such as paclitaxel.

SUMMARY OF THE INVENTION

While, as indicated above, pyridyl cyanoguanidines are promising antitumour agents with an extremely interesting activity profile, they are highly lipophilic and consequently sparingly soluble compounds and are, as such, generally available for oral administration only. However, many cancer patients are in a severely debilitated condition as a result of their illness giving rise to problems with patient compliance with respect to oral administration of drugs.

It is therefore an object of the present invention to provide pyridyl cyanoguanidines in the form of prodrugs with an improved solubility profile which prodrugs may be included in pharmaceutical compositions suitable for parenteral administration, i.e. liquid compositions in which the prodrug is dissolved in sufficient amounts to be converted to therapeutically effective quantities of the active compound on administration of the composition.

Furthermore, it has been found that pyridyl cyanoguanidine prodrugs exhibit an improved gastrointestinal absorption on oral administration. Consequently, it is another object of the invention to provide oral formulations of pyridyl cyanoguanidines as prodrugs with improved bioavailability.

Accordingly, the present invention relates to a compound of the general formula I

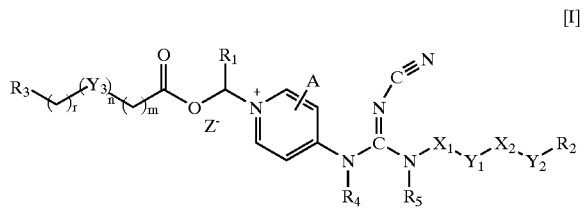

wherein
$X_1$ and $X_2$ independently represent a bond; a straight, branched and/or cyclic hydrocarbon diradical, optionally substituted with one or more hydroxy, halogen, nitro, amino, cyano, aminosulfonyl, alkylsulfonylamino, alkylcarbonyl, formyl, aminocarbonyl or alkylcarbonylamino; a heteroarylene or non-aromatic heterocyclic hydrocarbon diradical, all of which are optionally substituted with one or more straight, branched and/or cyclic non-aromatic hydrocarbon radical, hydroxyl, halogen, amino, nitro, cyano, aminosulfonyl, alkylsulfonylamino, alkylcarbonyl, formyl, aminocarbonyl or alkylcarbonylamino;

$Y_1$ and $Y_2$ independently represent a bond, an ether diradical (R'—O—R"), an amine diradical (R'—N—R"), O, S, S(O), S(O)$_2$, C(O), NH—CO, CO—NH, SO$_2$—N(R'), methylene or N(R')—SO$_2$ wherein R' and R" independently represent straight or branched hydrocarbon diradicals containing up to 4 carbon atoms;

$Y_3$ represents O, O—C(O), C(O)—O, N(R$_8$), R$_8$ being hydrogen or C$_{1-4}$alkyl $R_1$ represents hydrogen or straight, branched and/or cyclic alkyl, optionally substituted with phenyl; or an aromatic hydrocarbon radical;

$R_2$ represents aryl, heteroaryl or a non-aromatic heterocyclic hydrocarbon radical, all of which are optionally substituted; tetrahydropyranyloxy, di-(C$_{1-4}$ alkoxy) phosphinoyloxy or C$_{1-4}$ alkoxycarbonylamino;

$R_3$ represents hydrogen; a straight, branched and/or cyclic hydrocarbon radical, optionally substituted with one or more amino, hydroxy, carboxy, halogen, nitro, cyano, alkoxy, aminocarbonyl, C$_{1-4}$alkoxycarbonyl, C$_{1-4}$alkoxycarbonylamino, sulfo, hydroxysulfonyloxy, dihydroxyphosphinoyloxy, phosphono, sulfamino, aminosulfonyl, aminoacylamino or dialkoxyphosphinoyl; heteroaryl or a non-aromatic heterocyclic hydrocarbon radical, all of which are optionally substituted with one or more straight, branched and/or cyclic hydrocarbon radical, amino, hydroxy, carboxy, halogen, nitro, cyano, alkoxy, aminocarbonyl, C$_{1-4}$alkoxycarbonyl, C$_{1-4}$alkoxycarbonylamino, sulfo, hydroxysulfonyloxy, dihydroxyphosphinoyloxy, phosphono, sulfamino, aminosulfonyl, aminoacylamino or dialkoxyphosphinoyl;

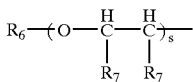

wherein s is an integer from 1 to 200; $R_6$ is hydrogen or an optionally substituted non-aromatic hydrocarbon radical; $R_7$ is independently hydrogen or methyl;

$R_4$ and $R_5$ independently represent hydrogen; a straight, branched and/or cyclic hydrocarbon radical, optionally substituted with halogen, hydroxyl, halogen, amino, nitro or cyano;

A represents hydrogen, an optionally substituted, straight, branched and/or cyclic hydrocarbon radical, hydroxy, halogen, nitro, cyano, heteroaryl, heteroaralkyl or thiol;

m and r are independently integers from 0 to 4; and n is 0 or 1;

$Z^-$ is a pharmaceutically acceptable anion, such as chloride, bromide, iodide, sulfate, methanesulfonate, p-toluenesulfonate, nitrate or phosphate.

Furthermore, the invention also relates to a compound of formula II, which is the free base form of the compounds of formula I, provided $R_4$ is hydrogen

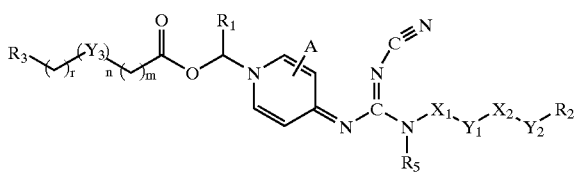

[II]

wherein A, $R_1$, $R_2$, $R_3$, $R_5$, $X_1$, $X_2$, $Y_1$, $Y_2$, $Y_3$, m, n and r are as indicated above.

It is understood that the compounds of the present invention include any tautomeric forms, optical isomers or diastereoisomers thereof. It is further understood that the invention includes pharmaceutically acceptable salts of compounds of formula I or II comprising basic or acidic groups.

On administration of a compound of formula I or formula II to a patient, the ester group $R_3$—$(CH_2)_r$—$(Y_3)_n$—$(CH_2)_m$—COOCHR$_1$— is hydrolysed enzymatically to liberate the active compound of formula III

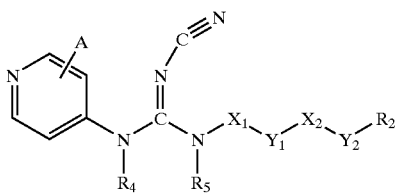

III wherein A, $R_2$, $R_4$, $R_5$, $X_1$, $X_2$, $Y_1$, and $Y_2$ are as indicated above, together with the aldehyde $R_1$CHO.

DETAILED DESCRIPTION OF THE INVENTION

DEFINITIONS

In the present context, the term "prodrug" is intended to indicate a derivative of an active compound which does not, or does not necessarily, exhibit the physiological activity of the active compound, but which may be subjected to enzymatic cleavage such as hydrolysis in vivo so as to release the active compound on administration of the prodrug. In this particular instance, the prodrug comprises the active compound which in itself is highly lipophilic provided with a side chain with predominantly hydrophilic properties imparting improved solubility characteristics to the prodrug, thereby making it more suitable for parenteral administration in the form of a solution or for oral administration to obtain an improved bioavailability. More specifically, the hydrophilic side chain selected for the compounds of the present invention comprises an ester group of formula $R_3$—$(CH_2)_r$—$(Y_3)_n$—$(CH_2)_m$—COOCHR$_1$— (wherein $R_3$, $R_1$, $Y_3$, m, n and r are as indicated above).

The term "alkyl" is intended to indicate a univalent radical derived from straight, branched or cyclic alkane by removing a hydrogen atom from any carbon atom. The term includes the subclasses primary, secondary and tertiary alkyl, such as methyl, ethyl, n-propyl, isopropyl, n-butyl, sec.-butyl, isobutyl, tert.-butyl, isopentyl, isohexyl, cyclohexyl, cyclopentyl and cyclopropyl.

The term "aryl" is intended to indicate radicals of carbocyclic aromatic rings, optionally fused bi-, tri- or tetracyclic rings wherein at least one ring is aromatic, e.g. phenyl, naphthyl, indanyl, indenyl, 1,4-dihydronaphtyl, flourenyl or tetralinyl.

The term "heteroaryl" is intended to indicate radicals of heterocyclic aromatic rings, in particular 5- or 6-membered rings with 1–3 heteroatoms selected from O, S and N, or optionally fused bicyclic rings, of which at least one is aromatic, with 1–4 heteroatoms, e.g. pyrrolyl, furanyl, thiophenyl, imidazolyl, oxazolyl, thiazolyl, pyrazolyl, pyridyl, pyrimidyl, purinyl, quinolinyl, chromenyl or carbazolyl.

The term "aralkyl" is intended to indicate an aromatic ring with an alkyl side chain, e.g. benzyl.

The term "halogen" is intended to indicate fluoro, chloro, bromo or iodo.

The term "aminosulfonyl" indicates a radical of the formula —S(O)$_2$NR$^a_2$, wherein each $R^a$ independently represents either hydrogen or alkyl.

The term "alkylsulfonylamino" indicates a radical of the formula —NR$^a_2$—S(O)$_2$—R$^b$, wherein each $R^a$ independently represents hydrogen or alkyl, and $R^b$ represents alkyl.

The term "alkylcarbonyl" indicates a radical of the formula —C(O)R$^b$, wherein $R^b$ is as just described.

The term "amino" indicates a radical of the formula —N(R$^a$)$_2$, wherein each $R^a$ independently represents hydrogen or alkyl.

The term "alkylcarbonylamino" indicates a radical of the formula —NR$^a$C(O)R$^b$, wherein $R^a$ and $R^b$ are as just described.

The term "alkoxy" indicates a radical of the formula OR$^b$, wherein $R^b$ is as just described.

The term "alkoxycarbonyl" is intended to indicate a radical of the formula —C(O)—OR$^b$, wherein $R^b$ is as indicated above.

The term "aminoacylamino" is intended to indicate a radical of the formula —NH—C(O)—R$^c$—NH$_2$, wherein $R^c$ is a diradical known from any natural amino acid, H$_2$N—R$^c$—COOH, or its enantiomer.

The term "aminocarbonyl" is intended to indicate a radical of the formula —C(O)—NR$^a_2$, wherein each $R^a$ independently represent hydrogen or alkyl.

The term "alkoxycarbonylamino" is intended to indicate a radical of the formula —NR$^a$—C(O)—OR$^b$, wherein $R^a$ and $R^b$ are as indicated above.

The term "hydrocarbon" is intended to indicate a compound comprising only hydrogen and carbon atoms, it may contain one or more double or triple carbon-carbon bonds, and it may comprise cyclic moieties in combination with branched or linear moieties. The term may be qualified as "non-aromatic heterocyclic", which is intended to indicate saturated or partly saturated cyclic compounds with 1–3 heteroatoms selected from O, S or N or optionally fused bicyclic rings with 1–4 heteroatoms, such as pyrrolidinyl, 3-pyrrolinyl, tetrahydrofuranyl, tetrahydrothiophenyl, piperidinyl, piperazinyl.

The term "pharmaceutically acceptable salt" is intended to indicate salts prepared by reacting a compound of formula I or II comprising a basic group with a suitable inorganic or organic acid, e.g. hydrochloric, hydrobromic, hydroiodic, sulfuric, nitric, acetic, phosphoric, lactic, maleic, phthalic, citric, propionic, benzoic, glutaric, gluconic, methanesulfonic, salicylic, succinic, tartaric, toluenesulfonic, sulfamic or fumaric acid. Pharmaceutically acceptable salts of compounds of formula II comprising an acidic group may be prepared by reaction with a suitable base such as sodium hydroxide, potassium hydroxide, ammonia or the like.

PREFERRED EMBODIMENTS OF THE COMPOUND OF FORMULA I OR II

In a preferred embodiment of the invention, $X_1$ and $Y_1$ are both bonds, while $X_2$ is a straight, branched or cyclic, saturated or unsaturated hydrocarbon diradical with 4 to 20 carbon atoms; $Y_2$ is O, S, C(O) or methylene; $R_2$ is optionally substituted aryl, heteroaryl, di-($C_{1-4}$alkoxy) phosphinoyloxy, $C_{1-4}$alkoxycarbonylamino or tetrahydropyranyloxy; $Y_3$ represents O or N($R_8$), wherein $R_8$ is hydrogen or $C_{1-4}$alkyl; $R_3$ is hydrogen, straight or branched $C_{1-6}$alkyl, $C_{3-6}$cycloalkyl, $C_{2-6}$alkenyl or $C_{2-6}$alkynyl, all of which are optionally substituted with amino, carboxy, aminocarbonyl or $C_{1-4}$alkoxycarbonyl; optionally substituted aryl, aralkyl, heteroaryl or

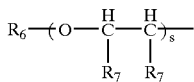

wherein s is an integer from 1 to 200;

$R_6$ is hydrogen or $C_{1-4}$alkyl;

$R_7$ is hydrogen or methyl;

$R_1$ is hydrogen, straight or branched $C_{1-4}$alkyl, aralkyl or aryl;

A, $R_4$ and $R_5$ are all hydrogen;

m and n are independently 0 or 1; r is 0;

and $Z^-$ is a pharmaceutically acceptable anion, such as chloride, bromide, iodide, sulfate, methanesulfonate, p-toluenesulfonate or nitrate.

In another embodiment of the compounds of formula I or II, m and n are 0, and $R_3$ is straight or branched $C_{1-6}$alkyl, optionally substituted with amino, hydroxy, carboxy, halogen, nitro, cyano, alkoxy, aminocarbonyl, $C_{1-4}$alkoxycarbonyl, $C_{1-4}$alkoxycarbonylamino, sulfo, hydroxysulfonyloxy, dihydroxyphosphinoyloxy, phosphono, sulfamino, aminosulfonyl, aminoacylamino or dialkoxyphosphinoyl.

In still another embodiment of the compounds of formula I or II, n is 1, m is 0, $Y_3$ is $NR_8$, wherein $R_8$ is as indicated above, and $R_3$ is hydrogen; straight or branched $C_{1-6}$alkyl, optionally substituted with amino, hydroxy, carboxy, halogen, nitro, cyano, alkoxy, aminocarbonyl, $C_{1-4}$alkoxycarbonyl, $C_{1-4}$alkoxycarbonylamino, sulfo, hydroxysulfonyloxy, dihydroxyphosphinoyloxy, phosphono, sulfamino, aminosulfonyl, aminoacylamino or dialkoxyphosphinoyl; or $R_3$ and $R_8$ together with the nitrogen atom of $Y_3$ form a 5-, 6- or 7-membered ring.

In a still further embodiment of the compounds of formula I or II, n is 1, m is 0, $Y_3$ is O, and $R_3$ is straight or branched $C_{1-6}$alkyl, optionally substituted with amino, hydroxy, carboxy, halogen, nitro, cyano, alkoxy, aminocarbonyl, $C_{1-4}$alkoxycarbonyl, $C_{1-4}$alkoxycarbonylamino, sulfo, hydroxysulfonyloxy, dihydroxyphosphinoyloxy, phosphono, sulfamino, aminosulfonyl, aminoacylamino or dialkoxyphosphinoyl.

In a still further embodiment of the compounds of formula I or II, n is 1, m is 0 or 1, $Y_3$ is O, and $R_3$ is $R_6$—(O—$CH_2$—$CH_2$)$_s$, wherein s is an integer from 1 to 150, in particular from 1 to 120, preferably from 1 to 80, more preferably from 1 to 50, such as from 1–30, e.g. from 1 to 20, and $R_6$ is hydrogen, methyl or ethyl. Particularly preferred in this embodiment, s is an integer from 2 to 10, such as 3, 4 or 5, and $R_6$ is methyl.

In a further preferred embodiment of the compounds of formula I or II, n is 1, m is 0, $Y_3$ is O, and $R_3$ is a 5, 6 or 7 membered non-aromatic heterocyclic hydrocarbon radical. Particular preferred in this embodiment, $R_3$ is pyrrolidinyl, piperidyl or hexahydro-1H-azepinyl.

In a preferred embodiment of the compounds of formula I or II, $R_2$ is optionally substituted aryl, in particular phenyl optionally substituted with one or more substituents selected from the group consisting of halogen, trifluoromethyl, hydroxy, $C_{1-4}$alkyl, $C_{1-4}$alkoxy, $C_{1-4}$alkoxycarbonyl, nitro, cyano, amino, aminocarbonyl, sulfamoyl or $C_{1-4}$hydroxyalkyl. A particular preferred substituent is halogen, such as chloro.

In a further preferred embodiment of the compounds of formula I or II, $X_1$ is a bond and $X_2$ is a $C_{4-12}$ hydrocarbon diradical, or $Y_1$ is a bond and $Y_2$ is O.

Examples of specific compounds of formula I are

| | Example No |
|---|---|
| 1-[2-(2-(2-Methoxyethoxy)-ethoxy)-ethoxy-carbonyloxymethyl]-4-[N'-cyano-N''-(6-(4-chlorophenoxy)-hexyl)-N-guanidino]-pyridinium chloride | 1 |
| 1-[2-(2-Methoxyethoxy)-ethoxy-carbonyloxymethyl]-4-[N'-cyano-N''-(6-(4-chlorophenoxy)-hexyl)-N-guanidino]-pyridinium chloride | 2 |
| 1-[2-Methoxyethoxy)-carbonyloxymethyl]-4-[N'-cyano-N''-(6-(4-chlorophenoxy)-hexyl)-N-guanidino]-pyridinium chloride | 3 |
| 1-[2-(2-(2-Methoxyethoxy)-ethoxy)-ethoxy-carbonyloxymethyl]-4-[N'-cyano-N''-(6-(4-chlorophenoxy)-hexyl)-N-guanidino]-pyridinium iodide | 4 |
| N-[1-(2-(2-(2-Methoxyethoxy)-ethoxy)-ethoxycarbonyloxymethyl)-1,4-dihydropyridin-4-ylidene]-N'-cyano-N''-(6-(4-chlorophenoxy)-hexyl)-guanidine | 5 |
| 1-[2-(2-(2-Methoxyethoxy)-ethoxy)-ethoxy-carbonyloxymethyl]-4-[N'-cyano-N''-(6-(4-chlorophenoxy)-hexyl)-N-guanidino]-pyridinium chloride | 6 |
| 1-[1-(2-(2-Methoxyethoxy)-ethoxy-carbonyloxy)-ethyl]-4-[N'-cyano-N''-(6-(4-chlorophenoxy)-hexyl)-N-guanidino]-pyridinium chloride | 7 |
| 1-[2-(2-(2-Methoxyethoxy)-ethoxy)-ethoxy-acetoxymethyl]-4-[N'-cyano-N''-(6-(4-chlorophenoxy)-hexyl)-N-guanidino]-pyridinium chloride | 8 |
| 1-[2-(2-(2-(2-Methoxyethoxy)-ethoxy)-ethoxy)- | 9 |

| | Example No |
|---|---|
| ethoxy-carbonyloxymethyl]-4-[N'-cyano-N"-(6-(4-chlorophenoxy)-hexyl)-N-guanidino]-pyridinium chloride | |
| 1-pivaloyloxymethyl-4-[N'-cyano-N"-(6-(4-chlorophenoxy)-hexyl)-N-guanidino]-pyridinium chloride | 10 |
| 1-Acetoxymethyl-4-[N'-cyano-N"-(6-(4-chlorophenoxy)-hexyl)-N-guanidino]-pyridinium chloride | 11 |
| 1-(L)-Valyloxymethyl-4-[N'-cyano-N"-(6-(4-chlorophenoxy)-hexyl)-N-guanidino]-pyridinium chloride, hydrochloride | 12 |
| 1-Glycyloxymethyl-4-[N'-cyano-N"-(6-(4-chlorophenoxy)-hexyl)-N-guanidino]-pyridinium chloride, hydrochloride | 13 |
| 1-[Monobenzyl succinyloxymethyl]-4-[N'-cyano-N"-(6-(4-chlorophenoxy)-hexyl)-N-guanidino]-pyridinium chloride | 14 |
| 1-[2-(2-(2-(2-(2-Methoxyethoxy)-ethoxy)-ethoxy)-ethoxy carbonyloxymethyl]-4-[N'-cyano-N"-(6-(4-chlorophenoxy)-hexyl)-N-guanidino]-pyridinium chloride | 15 |
| 1-[2-(2-(2-(2-(2-Methoxyethoxy)-ethoxy)-ethoxy-ethoxy-ethoxy-ethoxy-carbonyloxymethyl]-4-[N'-cyano-N"-(6-(4-chlorophenoxy)-hexyl)-N-guanidino]-pyridinium chloride | 16 |
| 1-[2-(2-(2-Methoxyethoxy)-ethoxy)-ethoxy-carbonyloxymethyl]-4-[N'-cyano-N"-(9-(diethoxyphosphinoyloxy)-nonyl)-N-guanidino]-pyridinium chloride | 17 |
| 1-[2-(2-(2-Methoxyethoxy)-ethoxy)-ethoxy-carbonyloxymethyl]-4-[N'-cyano-N"-(12-(tert-butyloxycarbonylamino)-dodecyl)-N-guanidino]-pyridinium iodide | 18 |
| 1-[2-(2-(2-Methoxyethoxy)-ethoxy)-ethoxy-carbonyloxymethyl]-4-[N'-cyano-N"-(12-(tert-butyloxycarbonylamino)-dodecyl)-N-guanidino]-pyridinium chloride | 19 |
| 1-[2-(2-(2-Methoxyethoxy)-ethoxy)-ethoxy-ethoxy-carbonyloxymethyl]-4-[N'-cyano-N"-(12-(tert-butyloxycarbonylamino)-dodecyl)-N-guanidino]-pyridinium chloride | 20 |
| 1-[3-(N-tert-butoxycarbonylamino)-propyloxy-carbonyloxymethyl]-4-[N'-cyano-N"-(6-(4-chlorophenoxy)-hexyl)-N-guanidino]-pyridinium iodide | 21 |
| 1-[3-Amino-propyloxy-carbonyloxymethyl]-4-[N'-cyano-N"-(6-(4-chlorophenoxy)-hexyl)-N-guanidino)-pyridinium chloride, hydrochloride | 22 |
| 1-[3-(N-tert-butoxycarbonylamino)-propyl-carbamoyloxymethyl]-4-[N'-cyano-N"-(6-(4-chlorophenoxy)-hexyl)-N-guanidino]-pyridinium iodide | 23 |
| 1-[3-Aminopropyl-carbamoyloxymethyl]-4-[N'-cyano-N"-(6-(4-chlorophenoxy)-hexyl)-N-guanidino]-pyridinium chloride, hydrochloride | 24 |
| 1-[5-(N-tert-butoxycarbonylamino)-pentanoyloxymethyl]-4-[N'-cyano-N"-(6-(4-chlorophenoxy)-hexyl)-N-guanidino]-pyridinium iodide | 25 |
| 1-[5-Amino-pentanoyloxymethyl]-4-[N'-cyano-N"-(6-(4-chlorophenoxy)-hexyl-N-guanidino]-pyridinium chloride, hydrochloride | 26 |
| 1-[3-(tert-butoxycarbonyl)-propionyloxymethyl]-4-[N'-cyano-N"-(6-(4-chlorophenoxy)-hexyl)-N-guanidino]-pyridinium chloride | 27 |
| 1-[3-carboxy-propionyloxymethyl]-4-[N'-cyano-N"-(6-(4-chlorophenoxy)-hexyl)-N-guanidino]-pyridinium chloride | 28 |
| 1-[N-(tert-butoxycarbonylmethyl)-carbamoyloxymethyl]-4-[N'-cyano-N"-(6-(4-chlorophenoxy)-hexyl)-N-guanidino]-pyridinium iodide | 29 |
| 1-[N-(carboxymethyl)-carbamoyloxymethyl]-4-[N'-cyano-N"-(6-(4-chlorophenoxy)-hexyl)-N-guanidino]-pyridinium chloride | 30 |
| 1-[1-(tert-butoxycarbonyl)-4-piperidyloxy-carbonyloxymethyl]-4-[N'-cyano-N"-(6-(4-chlorophenoxy)-hexyl)-N-guanidino]-pyridinium iodide | 31 |
| 1-[4-piperidyloxy-carbonyloxymethyl]-4-[N'-cyano-N"-(6-(4-chloro-phenoxy)-hexyl)-N-guanidino]-pyridinium chloride, hydrochloride | 32 |
| 1-[tert-butoxycarbonylmethoxy-carbonyloxymethyl]-4-[N'-cyano-N"-(6-(4-chlorophenoxy)-hexyl)-N-guanidino]-pyridinium iodide | 33 |
| 1-[carboxymethoxy-carbonyloxymethyl]-4-[N'-cyano-N"-(6-(4-chlorophenoxy)-hexyl)-N-guanidino]-pyridinium chloride | 34 |
| N-[1-(α-(2-(2-(2-Methoxyethoxy)-ethoxy)-ethoxycarbonyloxy)benzyl)-1,4-dihydropyridin-4-ylidene]-N'-cyano-N"-(6-(4-chlorophenoxy)-hexyl)-guanidine | 35 |

GENERAL METHODS OF PREPARATION

Compounds of formula I may be prepared by reacting a compound of formula III

III wherein A, $R_2$, $R_4$, $R_5$, $X_1$, $X_2$, $Y_1$ and $Y_2$ are as indicated above, with a compound of formula IV

IV wherein $R_1$, $R_3$, $Y_3$, m, n and r are as indicated above, and B is a leaving group, such as Cl, Br or I. In addition $R_3$ and $Y_3$ may optionally contain protecting groups.

The reaction of a compound of formula III with a compound of formula IV may be performed in a solvent-free environment or in an inert solvent such as acetonitrile at a temperature between room temperature and 150° C. to afford a compound of formula I optionally after removal of protecting groups.

The compounds of formula IV are known from the literature or may be prepared by methods well known to persons skilled in the art, e.g. by reacting a carboxylic halide of formula V $$R_3-(CH_2)_r-(Y_3)_n-(CH_2)_m-C(=O)-B \quad V$$

wherein $R_3$, $Y_3$, B, m, n and r are as indicated in formula IV, with the proviso that m is different from 0 when n is 1, with an aldehyde of formula VI $$R_1-C(=O)-H \quad VI$$

wherein $R_1$ is as indicated above, optionally in the presence of a catalyst such as anhydrous zinc chloride or anhydrous aluminium chloride.

When n is 1 and m is 0, compounds of formula IV may be prepared by reacting a compound of formula VII

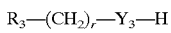

wherein $R_3$, $Y_3$ and r are as indicated in formula IV, with a compound of formula VIII

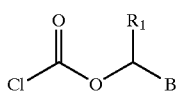

wherein $R_1$ and B are as indicated above.

The reaction between a compound of formula VII and a compound of formula VIII may be performed at a temperature between room temperature and —70° C. in an inert organic solvent, such as dichloromethane, in the presence of a suitable base such as pyridine.

In another method compounds of formula IV in which B is chlorine are prepared by reacting a compound of formula IX

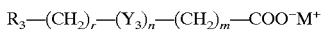

wherein $R_3$, $Y_3$, m, n and r are as indicated in formula V and $M^+$ is suitable metal cation, e.g. an alkalimetal cation, or a tertiary ammonium ion, with a compound of formula X.

wherein $R_1$ is as indicated above and X is iodo bromo or chlorosulfonyloxy.

The reaction between IX and X may be performed in a suitable solvent such as dimethylformamide at a suitable temperature, e.g. at room temperature, when X is iodo or bromo. When X is chlorosulfonyloxy the reaction may be performed under phase transfer conditions as described in *Synthetic Communications* 14, 857–864 (1984).

Compounds of formula IV in which B is chloro may be transformed into the corresponding compounds in which B is iodo by reaction with sodium iodide in acetone or acetonitrile.

The compounds of formulae V, VI, VII, VIII, IX and X are either known from the literature or may be prepared by methods well known to persons skilled in the art.

Compounds of formula III are known from the literature and may be prepared by any one of the methods disclosed in, for instance, EP 660 823, WO 98/54141, WO 98/54143, WO 98/54144, WO 98/54145, WO 00/61559 and WO 00/61561.

A compound of formula I, provided that $R_4$ is hydrogen may be converted into the corresponding free base of formula II by treating a solution of a compound of formula I in an appropriate inert solvent, e.g. dichloromethane, with a suitable base, e.g. aqueous sodium bicarbonate. The free base of formula II may be reconverted into a salt of formula I by treating a solution of a compound of formula II in an appropriate inert solvent, e.g. dichloromethane, with a suitable acid of formula ZH, wherein Z is as indicated above.

Pharmaceutical Compositions

In another aspect, the invention relates to pharmaceutical formulations of a compound of formula I or II intended for the treatment of proliferative diseases. The formulations of the present invention, both for veterinary and for human medical use, comprise active ingredients in association with a pharmaceutically acceptable carrier(s) and optionally other therapeutic ingredient(s). The carrier(s) must be "acceptable" in the sense of being compatible with the other ingredients of the formulations and not deleterious to the recipient thereof.

Conveniently, the active ingredient comprises from 0.1–100% by weight of the formulation. Conveniently, a dosage unit of a formulation contain between 0.07 mg and 1 g of a compound of formula I or II.

By the term "dosage unit" is meant a unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers.

The formulations include e.g. those in a form suitable for oral (including sustained or timed release), rectal, parenteral (including subcutaneous, intraperitoneal, intramuscular, intraarticular and intravenous), transdermal, ophthalmic, topical, nasal or buccal administration.

The formulations may conveniently be presented in dosage unit form and may be prepared by any of the methods well known in the art of pharmacy, e.g. as disclosed in Remington, *The Science and Practice of Pharmacy*, 20$^{th}$ ed., 2000. All methods include the step of bringing the active ingredient into association with the carrier, which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units, such as capsules, sachets, tablets or lozenges, each containing a predetermined amount of the active ingredient; in the form of a powder or granules; in the form of a solution or a suspension in an aqueous liquid or non-aqueous liquid, such as ethanol or glycerol; or in the form of an oil-in-water emulsion or a water-in-oil emulsion. Such oils may be edible oils, such as e.g. cottonseed oil, sesame oil, coconut oil or peanut oil. Suitable dispersing or suspending agents for aqueous suspensions include synthetic or natural gums such as tragacanth, alginate, acacia, dextran, sodium carboxymethylcellulose, gelatin, methylcellulose, hydroxypropylmethylcellulose, hydroxypropylcellulose, carbomers and polyvinylpyrrolidone. The active ingredients may also be administered in the form of a bolus, electuary or paste.

A tablet may be made by compressing or moulding the active ingredient optionally with one or more accessory ingredients. Compressed tablets may be prepared by compressing, in a suitable machine, the active ingredient(s) in a free-flowing form such as a powder or granules, optionally mixed by a binder, such as e.g. lactose, glucose, starch, gelatine, acacia gum, tragacanth gum, sodium alginate, carboxymethylcellulose, methylcellulose, hydroxypropylmethylcellulose, polyethylene glycol, waxes or the like; a lubricant such as e.g. sodium oleate, sodium stearate, magnesium stearate, sodium benzoate, sodium acetate, sodium chloride or the like; a disintegrating agent such as e.g. starch, methylcellulose, agar, bentonite, croscarmellose sodium, sodium starch glycollate, crospovidone or the like or a dispersing agent, such as polysorbate 80. Moulded tablets may be made by moulding, in a suitable machine, a mixture of the powdered active ingredient and suitable carrier moistened with an inert liquid diluent.

Formulations for rectal administration may be may in the form of suppositories in which the compound of the present invention is admixed with low melting water soluble or insoluble solids such as cocoa butter, hydrogenated vegetable oils, polyethylene glycol or fatty acids esters of polyethylene glycols, while elixirs may be prepared using myristyl palmitate.

Formulations suitable for parenteral administration conveniently comprise a sterile oily or aqueous preparation of the active ingredients, which is preferably isotonic with the blood of the recipient, e.g. isotonic saline, isotonic glucose solution or buffer solution. The formulation may be conveniently sterilised by for instance filtration through a bacteria retaining filter, addition of sterilising agent to the formulation, irradiation of the formulation or heating of the formulation. Liposomal formulations as disclosed in e.g. *Encyclopedia of Pharmaceutical Technology*, vol.9, 1994, are also suitable for parenteral administration.

Alternatively, the compound of formula I may be presented as a sterile, solid preparation, e.g. a freeze-dried powder, which is readily dissolved in a sterile solvent immediately prior to use.

Transdermal formulations may be in the form of a plaster or a patch.

Formulations suitable ophthalmic administration may be in the form of a sterile aqueous preparation of the active ingredients, which may be in microcrystalline form, for example, in the form of an aqueous microcrystalline suspension. Liposomal formulations or biodegradable polymer systems e.g. as disclosed in *Encyclopedia of Pharmaceutical Technology*, vol.2, 1989, may also be used to present the active ingredient for ophthalmic administration.

Formulations suitable for topical or ophthalmic administration include liquid or semi-liquid preparations such as liniments, lotions, gels, applicants, oil-in-water or water-in-oil emulsions such as creams, ointments or pastes; or solutions or suspensions such as drops.

Formulations suitable for nasal or buccal administration include powder, self-propelling and spray formulations, such as aerosols and atomisers.

In addition to the aforementioned ingredients, the formulations of a compound of formula I or II may include one or more additional ingredients such as diluents, buffers, flavouring agents, colourant, surface active agents, thickeners, preservatives, e.g. methyl hydroxybenzoate (including antioxidants), emulsifying agents and the like.

In the systemic treatment using the present invention daily doses of from 0.001–500 mg per kilogram body weight, preferably from 0.002–100 mg/kg of mammal body weight, for example 0.003–20 mg/kg or 0.003 to 5 mg/kg of a compound of formula I or II is administered, typically corresponding to a daily dose for an adult human of from 0.01 to 37000 mg. However, the present invention also provides compounds and compositions intended for administration with longer intervals, e.g. every week, every three weeks or every month. In the topical treatment of dermatological disorders, ointments, creams or lotions containing from 0.1–750 mg/g, and preferably from 0.1–500 mg/g, for example 0.1–200 mg/g of a compound of formula I or II is administered. For topical use in ophthalmology ointments, drops or gels containing from 0.1–750 mg/g, and preferably from 0.1–500 mg/g, for example 0.1–200 mg/g of a compound of formula I or II is administered. The oral compositions are formulated, preferably as tablets, capsules, or drops, containing from 0.07–1000 mg, preferably from 0.1–500 mg, of a compound of formula I or II per dosage unit.

In a preferred embodiment, the invention provides pharmaceutical compositions comprising a compound of formula I or II in combination with one or more other pharmacologically active compounds used in the treatment of proliferative diseases. Examples of compounds used in the treatment of proliferative diseases which may be used together with compounds of the present invention include S-triazine derivatives such as altretamine; enzymes such as asparaginase; antibiotic agents such as bleomycin, dactinomycin, daunorubicin, doxorubicin, idarubicin, mitomycin, epirubicin and plicamycin; alkylating agents such as busulfan, carboplatin, carmustine, chlorambucil, cisplatin, cyclophosphamide, dacarbazine, ifosfamide, lomustine, mechlorethamine, melphalan, procarbazine and thiotepa; antimetabolites such as cladribine, cytarabine, floxuridine, fludarabine, fluorouracil, hydroxyurea, mercaptopurine, methotrexate, gemcitabin, pentostatin and thioguanine; antimitotic agents such as etoposide, paclitaxel, teniposide, vinblastine, vinorelbin and vincristine; hormonal agents, e.g. aromatase inhibitors such as aminoglutethimide, corticosteroids, such as dexamethasone and prednisone, and luteinizing hormone releasing hormone (LH-RH); antiestrogens such as tamoxifen, formestan and letrozol; antiandrogens such as flutamide; biological response modifiers, e.g. lymphokines such as aldesleukin and other interleukines; interferon such as interferon-α; growth factors such as erythropoietin, filgrastim and sagramostim; differentiating agents such as vitamin D derivatives and all-trans retinoic acid; immunoregulators such as levamisole; and monoclonal antibodies, tumour necrosis factor α and angiogenesis inhibitors. Finally, ionising radiation, although not readily defined as a compound, is heavily depended on in the treatment of neoplastic diseases, and may be combined with the compounds of the present invention. Due to the severe side effects often experienced by patients receiving anti-neoplastic treatment it is often desirable also to administer therapeutica which are not themselves anti-neoplastic, but rather help relieving the side effects. Such compounds include amifostin, leucovorin and mesna.

In particular, anti-neoplastic compounds, such as paclitaxel, fluorouracil, etoposide, cyclophospamide, cisplatin, carboplatin, vincristine, gemcitabine, vinorelbine, chlorambucil, doxorubicin and melphalan appear beneficial in the combination compositions of the present invention.

It is envisaged that the combination composition of the present invention may be provided as mixtures of the compounds or as individual compounds intended for simultaneous or sequential administration. It lies within the capabilities of a skilled physician or veterinarian to decide time intervals in a sequential administration regime.

In a further aspect, the invention relates to a method of treating or ameliorating proliferative diseases or conditions, the method comprising administering, to a patient in need thereof, a pharmaceutical composition comprising a compound of formula I or II, which compound is hydrolysed enzymatically upon administration to provide a compound of formula III, in an amount sufficient to effect treatment or amelioration of said proliferative disease or condition, optionally together with another anti-neoplastic compound and/or ionising radiation.

In particular, proliferative diseases or conditions to be treated by the present method include a variety of cancers and neoplastic diseases or conditions including leukaemia, acute myeloide leukaemia, chronic myeloide leukaemia, chronic lymphatic leukaemia, myelodysplasia, multiple myeloma, Hodgkin's disease or non-Hodgkin's lymphoma, small or non-small cell lung carcinoma, gastric, intestinal or colorectal cancer, prostate, ovarian or breast cancer, head, brain or neck cancer, cancer in the urinary tract, kidney or bladder cancer, malignant melanoma, liver cancer, uterine or pancreatic cancer.

The invention also relates to the use of compounds of formula I or II, optionally together with other anti-neoplastic compounds, as indicated above, in the manufacture of medicaments. In particular, said medicament is intended to be used for the treatment of proliferative diseases, e.g. cancers as mentioned above.

As indicated above, it is preferred to administer the compounds of the invention parenterally, such as in a liquid, preferably aqueous, solution intended for intravenous injection or infusion. A suitable dosage of the compound of the invention will depend, inter alia, on the age and condition of the patient, the severity of the disease to be treated and other factors well known to the practising physician. The compound may be administered either orally or parenterally according to different dosing schedules, e.g. daily or with weekly intervals. In general a single dose will be in the range from 0.1 to 400 mg/kg bodyweight. Parenterally, the compound may be administered as a bolus (i.e. the entire dose is administered at once) or in divided doses two or more times a day or preferably as an intravenous infusion.

The invention is described in further detail in the following examples which are not in any way intended to limit the scope of the invention as claimed.

EXAMPLES

For $^1$H nuclear magnetic resonance (NMR) spectra (300 MHz) and $^{13}$C NMR (75.6 MHz) chemical shift values are quoted relative to internal tetramethylsilane ($\delta$=0.00) or chloroform ($\delta$=7.25) or deuteriochloroform ($\delta$=76.81 for $^{13}$C NMR) standards. The value of a multiplet, either defined (singlet (s), doublet (d), triplet (t), quartet (q)) or not (broad (br)), at the approximate midpoint is given unless a range is quoted. The organic solvents used were anhydrous.

Preparation 1

Chloromethyl 2-(2-(2-methoxyethoxy)-ethoxy)-ethyl carbonate

Chloromethyl chloroformate (2.94 ml) was added to an ice-cold solution of triethyleneglycol monomethylether (4.70 ml) in dichloromethane (30 ml) followed by pyridine (2.93 ml) at such a rate that the temperature was kept below 10° C. After stirring overnight at room temperature the reaction mixture was washed twice with 0.5 M HCl followed by water and aqueous sodium bicarbonate. Drying over magnesium sulfate, filtration, evaporation in vacuo followed by distillation in vacuo, b.p.: 102–108° C. at 0.03 mbar, afforded the title compound as a colourless oil.

$^1$H NMR (CDCl$_3$) $\delta$=5.73 (s,2H), 4.37 (m,2H), 3.75 (m,2H), 3.70–3.60 (m,6H), 3.55 (m,2H), 3.38 (s,3H)

Preparation 2

Chloromethyl 2-(2-methoxyethoxy)-ethyl carbonate

This compound was prepared by following the procedure described in Preparation 1 but substituting diethylene glycol monomethylether for triethyleneglycol monomethylether. Colourless oil, b.p.: 80–82° C. at 0.03 mbar.

$^1$H NMR (CDCl$_3$) $\delta$=5.74 (s,2H), 4.38 (m,2H), 3.75 (m,2H), 3.66 (m,2H), 3.55 (m,2H), 3.38 (s,3H)

Preparation 3

Chloromethyl 2-methoxyethyl carbonate

This compound was prepared by following the procedure described in Preparation 1 but substituting ethylene glycol monomethylether for triethyleneglycol monomethylether. Colourless oil, b.p.: 36° C. at 0.03 mbar.

$^1$H NMR (CDCl$_3$) $\delta$=5.74 (s,2H), 4.37 (m,2H), 3.64 (m,2H), 3.40 (s,3H)

Preparation 4

1-Chloroethyl 2-(2-methoxyethoxy)-ethyl carbonate

This compound was prepared by following the procedure described in Preparation 1 but substituting diethylene glycol monomethylether for triethyleneglycol monomethylether and 1-chloroethyl chloroformate for chloromethyl chloroformate. Colourless oil, b.p.: 82–88° C. at 0.03 mbar.

$^{13}$C NMR (CDCl$_3$) $\delta$=152.9, 84.6, 71.9, 70.6, 68.7, 67.8, 59.1, 25.2

Preparation 5

Iodomethyl 2-(2-(2-methoxyethoxy)-ethoxy)-ethyl carbonate

Chloromethyl 2-(2-(2-methoxyethoxy)-ethoxy)-ethyl carbonate (9 g) was added to a solution of sodium iodide (21.07 g) in acetone (45 ml). After stirring at 40° C. for 2.5 hours the reaction mixture was cooled in ice, filtered and evaporated in vacuo. The residue was taken up in dichloromethane, washed with aqueous sodium bicarbonate and sodium thiosulfate, dried over magnesium sulfate, filtered and evaporated in vacuo. Purification on silica gel with petroleum ether/ethyl acetate (1:1) as eluent gave the title compound as a light yellow oil.

$^1$H NMR (CDCl$_3$) $\delta$=5.95 (s,2H), 4.37 (m,2H), 3.74 (m,2H), 3.7–3.5 (m,8H), 3.38 (s,3H)

Preparation 6

1-Iodoethyl 2-(2-methoxyethoxy)-ethyl carbonate

This compound was prepared as described in Preparation 5 but substituting 1-chloroethyl 2-(2-methoxyethoxy)-ethyl carbonate for chloromethyl 2-(2-(2-methoxyethoxy)-ethoxy)-ethyl carbonate. The resulting oil contained 35% of the title compound and 65% of the starting material. This mixture was used in the next step without further purification.

Preparation 7

Chloromethyl 2-(2-(2-methoxyethoxy)-ethoxy)-ethoxy-acetate

This compound was prepared from 2-(2-(2-methoxyethoxy)-ethoxy)-ethoxy-acetic acid and chloromethyl chlorosulfate as described in the general procedure given in Synthetic Communications 14, 857–864 (1984). The resulting oil was purified by distillation in vacuo, b.p.: 130–132° C. at 0.06 mbar.

$^{13}$C NMR (CDCl$_3$) $\delta$=168.8, 72.0, 71.1, 70.7, 70.6, 70.6, 70.6, 68.6, 68.5, 59.0

Preparation 8

Chloromethyl 2-(2-(2-(2-methoxyethoxy)-ethoxy)-ethoxy)-ethyl carbonate

Prepared as described in Preparation 1 but substituting tetraethyleneglycol monomethylether for triethyleneglycol monomethylether. Yellow oil.

$^{13}$C NMR (CDCl$_3$) $\delta$=153.4, 72.2, 72.0, 70.7, 70.7, 70.6, 70.5, 68.6, 68.1, 59.0

Preparation 9

Iodomethyl 2-(2-(2-(2-methoxyethoxy)-ethoxy)-ethoxy)-ethyl carbonate

Prepared as described in Preparation 5 but substituting chloromethyl 2-(2-(2-(2-methoxyethoxy)-ethoxy)-ethoxy)-ethyl carbonate for chloromethyl 2-(2-(2-methoxyethoxy)-ethoxy)-ethyl carbonate. Reddish-yellow oil which was used in the next step without further purification.

$^1$H NMR (CDCl$_3$) δ=5.95 (s,2H), 4.36 (m,2H), 3.74 (m,2H), 3.70–3.50 (m,12H), 3.38 (s,3H)

Preparation 10

Chloromethyl benzyl succinate

Prepared as described in Preparation 7 but substituting succinic acid monobenzylester for 2-(2-(2-methoxyethoxy)-ethoxy)-ethoxy-acetic acid. The resulting oil was purified by distillation in vacuo, b.p.: 145–151° C. at 0.4 mbar.

$^{13}$C NMR (CDCl$_3$) δ=171.6, 170.4, 135.6, 128.6, 128.4, 128.3, 68.8, 66.7, 29.0, 28.8

Preparation 11

N-tert-butoxycarbonyl-(L)-valine chloromethyl ester

Prepared as described in Preparation 7 but substituting N-tert-butoxycarbonyl-(L)-valine for 2-(2-(2-methoxyethoxy)-ethoxy)-ethoxy-acetic acid. The resulting oil was purified by chromatography on silica gel.

$^1$H NMR (CDCl$_3$) δ=5.87 (1H,d), 5.62 (1H,d), 5.0 (1H, br), 4.27 (1H,m), 2.17 (1H,m), 1.45 (9H,s), 1.00 (3H,d), 0.93 (3H,d)

Preparation 12

N-tert-butoxycarbonyl-glycine chloromethyl ester

Prepared as described in Preparation 7 but substituting N-tert-butoxycarbonyl-glycine for 2-(2-(2-methoxyethoxy)-ethoxy)-ethoxyacetic acid.

$^1$H NMR (CDCl$_3$) δ=5.75 (2H,s), 5.05 (1H,br), 3.99 (2H,d), 1.46 (9H,s)

Preparation 13

Chloromethyl 2-(2-(2-(2-methoxyethoxy)-ethoxy)-ethoxy)-ethyl carbonate

Prepared as described in Preparation 1 but substituting pentaethyleneglycol monomethylether for triethyleneglycol monomethylether. Yellow oil.

$^1$H NMR (CDCl$_3$) δ=5.73 (s, 2H), 4.37 (m, 2H), 3.74 (m, 2H), 3.65 (m, 14H), 3.55 (m, 2H), 3.38 (s, 3H)

Preparation 14

Chloromethyl 2-(2-(2-(2-(2-methoxyethoxy)-ethoxy)-ethoxy)-ethoxy)-ethyl carbonate Prepared as described in Preparation 1 but substituting hexaethyleneglycol monomethylether for triethyleneglycol monomethylether. Yellow oil.

$^1$H NMR (CDCl$_3$) δ=5.74 (s, 2H), 4.37 (m, 2H), 3.75 (m, 2H), 3.65 (m, 18H), 3.53 (m, 2H), 3.38 (s, 3H)

Preparation 15

Iodomethyl 2-(2-(2-(2-methoxyethoxy)-ethoxy)-ethoxy)-ethyl carbonate

Prepared as described in Preparation 5 but substituting chloromethyl 2-(2-(2-(2-methoxyethoxy)-ethoxy)-ethoxy)-ethyl carbonate for chloromethyl 2-(2-(2-methoxyethoxy)-ethoxy)-ethyl carbonate. Purification on silica gel with petroleum ether/ethyl acetate (1:1) as eluent gave the title compound as a light yellow oil.

$^1$H NMR (CDCl$_3$) δ=5.95 (s, 2H), 4.36 (m, 2H), 3.74 (m, 2H), 3.65 (m, 14H), 3.64 (m, 2H), 3.38 (s, 3H)

Preparation 16

Iodomethyl 2-(2-(2-(2-(2-methoxyethoxy)-ethoxy)-ethoxy)-ethoxy)-ethyl carbonate

Prepared as described in Preparation 5 but substituting chloromethyl 2-(2-(2-(2-(2-methoxyethoxy)-ethoxy)-ethoxy)-ethoxy)-ethyl carbonate for chloromethyl 2-(2-(2-methoxyethoxy)-ethoxy)-ethyl carbonate. Purification on silica gel with petroleum ether/ethyl acetate (1:1) as eluent gave the title compound as a light yellow oil.

$^1$H NMR (CDCl$_3$) δ=5.95 (s, 2H), 4.36 (m, 2H), 3.74 (m, 2H), 3.65 (m, 18H), 3.55 (m, 2H), 3.38 (s, 3H)

Preparation 17

Chloromethyl 3-(N-tert-butoxycarbonylamino)-propyl carbonate

Prepared as described in Preparation 1 but substituting 3-(N-tert-butoxycarbonylamino)-propanol for triethyleneglycol monomethylether. Colourless oil.

$^1$H NMR (CDCl$_3$) δ=5.73 (s, 2H), 4.7 (Br, 1H), 4.29 (t, 2H), 3.22 (q, 2H), 1.90 (m, 2H), 1.44 (s, 9H)

Preparation 18

Iodomethyl 3-(N-tert-butoxycarbonylamino)-propyl carbonate

Prepared as described in Preparation 5 but substituting chloromethyl 3-(N-tert-butoxycarbonylamino)-propyl carbonate for chloromethyl 2-(2-(2-methoxyethoxy)-ethoxy)-ethyl carbonate. The resulting yellow oil was purified by chromatography on silica gel with petroleum ether/ethyl acetate (2:1) as eluent. Light yellow oil.

$^1$H NMR (CDCl$_3$) δ=5.95 (s, 2H), 4.68 (Br, 1H), 4.29 (t, 2H), 3.21 (q, 2H), 1.89 (m, 2H), 1.44 (s, 9H)

Preparation 19

Chloromethyl N-(3-(N-tert-butoxycarbonylamino)-propyl)-carbamate

A solution of chloromethyl chloroformate (2.84 g) in dichloromethane (10 ml) was added dropwise with stirring to an ice-cold solution of 3-(N-tert-butoxycarbonylamino)-propylamine (3.49 g) and diisopropylethylamine (3.10 g) in dichloromethane (30 ml). After stirring for a further 3 hours at room temperature, the mixture was extracted with ice-cold 0.5 M hydrochloric acid followed by water and aqueous sodium bicarbonate. Drying over magnesium sulfate and evaporation in vacuo gave the title compound as colourless crystals.

$^1$H NMR (CDCl$_3$) δ=5.75 (s, 2H), 5.74 (Br, 1H), 4.77 (Br, 1H), 3.27 (q, 2H), 3.19 (q, 2H), 1.65 (m, 2H), 1.44 (s, 9H)

Preparation 20

Iodomethyl N-(3-(N-tert-butoxycarbonylamino)-propyl)-carbamate

A solution of chloromethyl N-(3-(N-tert-butoxycarbonylamino)-propyl)carbamate (2 g) and sodium iodide (4.5 g) in acetonitrile (15 ml) was stirred for 1 hour at room temperature, evaporated in vacuo, redissolved in dichloromethane and filtered. The filtrate was evaporated in vacuo and the residue was purified by chromatography on silica gel with ethyl acetate/hexane (1:2) as eluent to yield the title compound as colourless crystals.

$^1$H NMR (CDCl$_3$) δ=5.97 (s, 2H), 5.65 (Br, 1H), 4.77 (Br, 1H), 3.26 (q, 2H), 3.19 (q, 2H), 1.66 (m, 2H), 1.44 (s, 9H)

Preparation 21

Chloromethyl 5-(N-tert-butoxycarbonylamino)-pentanoate

This compound was prepared as described in Preparation 7 but substituting 5-(N-tert-butoxycarbonylamino)-pentanoic acid for 2-(2-(2-methoxyethoxy)-ethoxy)-acetic acid. The crude material was distributed between diethyl ether and water. The organic phase was separated and dried over magnesium sulfate. Evaporation in vacuo gave a colourless oil which was used in the next step without further purification.

$^1$H NMR (CDCl$_3$) δ=5.70 (s, 2H), 4.6 (Br, 1H), 3.13 (q, 2H), 2.42 (t, 2H), 1.69 (m, 2H), 1.53 (m, 2H), 1.44 (s, 9H)

Preparation 22

Iodomethyl 5-(N-tert-butoxycarbonylamino)-pentanoate

Prepared as described in Preparation 5 but substituting chloromethyl 5-(N-tert-butoxycarbonylamino)-pentanoate for chloromethyl 2-(2-(2-methoxyethoxy)-ethoxy)-ethyl carbonate. Colourless oil which crystallised in the freezer.

$^1$H NMR (CDCl$_3$) δ=5.90 (s, 2H), 4.55 (q, 1H), 3.12 (q, 2H), 2.36 (t, 2H), 1.66 (m, 2H), 1.52 (m, 2H), 1.44 (s, 9H)

Preparation 23

Chloromethyl tert-butyl succinate

Prepared as described in Preparation 7 but substituting mono-tert-butyl succinate for 2-(2-(2-methoxyethoxy)-ethoxy)-acetic acid. The crude product was purified by chromatography on silica gel with petroleum ether/ethyl acetate (9:1) as eluent.

$^1$H NMR (CDCl$_3$) δ=5.71 (s, 2H), 2.7–2.5 (m, 4H), 1.45 (s, 9H)

Preparation 24

Chloromethyl N-(tert-butoxycarbonylmethyl)-carbamate

A solution of chloromethyl chloroformate (1.69 g) in dichloromethane (5 ml) was added dropwise with stirring to an ice-cold solution of tert-butyl glycinate, hydrochloride (2.0 g) and diisopropylethylamine (3.7 g) in dichloromethane (20 ml). After stirring for a further 2 hours at room temperature, the mixture was extracted with ice-cold 0.5 M hydrochloric acid followed by water and aqueous sodium bicarbonate. Drying over magnesium sulfate and evaporation in vacuo gave the title compound as a colourless powder.

$^1$H NMR (CDCl$_3$) δ=5.75 (s, 2H), 5.42 (Br, 1H), 3.91 (d, 2H), 1.48 (s, 9H)

Preparation 25

Iodomethyl N-(tert-butoxycarbonylmethyl)-carbamate

Prepared as described in Preparation 20 but substituting chloromethyl N-(tert-butoxycarbonylmethyl)-carbamate for chloromethyl N-(3-(N-tert-butoxycarbonylamino)-propyl)-carbamate. Light yellow powder.

$^1$H NMR (CDCl$_3$) δ=5.97 (s, 2H), 5.34 (Br, 1H), 3.88 (d, 2H), 1.47 (s, 9H)

Preparation 26

Chloromethyl 1-(tert-butoxycarbonyl)-4-piperidyl carbonate

Prepared as described in Preparation 1 but substituting 1-(tert-butoxycarbonyl)-4-hydroxy-piperidine for triethyleneglycol monomethylether. Light red oil.

$^1$H NMR (CDCl$_3$) δ=5.73 (s, 2H), 4.88 (m, 1H), 3.71 (m, 2H), 3.26 (m, 2H), 1.93 (m, 2H), 1.72 (m, 2H), 1.46 (s, 9H)

Preparation 27

Iodomethyl 1-(tert-butoxycarbonyl)-4-piperidyl carbonate

Prepared as described in Preparation 5 but substituting chloromethyl 1-(tert-butoxycarbonyl)-4-piperidyl carbonate for chloromethyl 2-(2-(2-methoxyethoxy)-ethoxy)-ethyl carbonate. The resulting oil was purified by chromatography on silica gel with hexane/ethyl acetate (3:1) as eluent. Yellow oil.

$^1$H NMR (CDCl$_3$) δ=5.95 (s, 2H), 4.87 (m, 1H), 3.71 (m, 2H), 3.26 (m, 2H), 1.93 (m, 2H), 1.71 (m, 2H), 1.46 (s, 9H)

Preparation 28

Chloromethyl tert-butoxycarbonylmethyl carbonate

Prepared as described in Preparation 1 but substituting tert-butyl glycolate for triethyleneglycol monomethylether. Colourless oil.

$^1$H NMR (CDCl$_3$) δ=5.76 (s, 2H), 4.58 (s, 2H), 1.49 (s, 9H)

Preparation 29

Iodomethyl tert-butoxycarbonylmethyl carbonate

Chloromethyl tert-butoxycarbonylmethyl carbonate (6.45 g) was added to a solution of sodium iodide (16.5 g) in acetonitril (65 ml). After stirring at 40° C. for 4 hours the reaction mixture was cooled in ice, filtered and evaporated in vacuo. The residue was taken up in dichloromethane, washed with aqueous sodium bicarbonate and sodium thiosulfate, dried over magnesium sulfate, filtered and evaporated in vacuo. Purification on silica gel with hexane/ethyl acetate (3:1) as eluent gave the title compound as a colourless oil.

$^1$H NMR (CDCl$_3$) δ=5.98 (s, 2H), 4.56 (s, 2H), 1.49 (s, 9H)

Preparation 30

α-Chlorobenzyl 2-(2-(2-methoxyethoxy)-ethoxy)-ethyl carbonate

α-Chlorobenzyl chloroformate (1 g) was added to an ice-cold solution of triethyleneglycol monomethylether (0.7 ml) in dichloromethane (5 ml) followed by pyridine (0.43 ml) at such a rate that the temperature was kept below 10° C. After stirring overnight at room temperature the reaction mixture was washed twice with 0.5 M HCl followed by water and aqueous sodium bicarbonate. Drying over magnesium sulfate, filtration, evaporation in vacuo followed by chromatography on silica gel with hexane/ethyl acetate (1:1) as eluent gave the title compound as a colourless oil.

$^1$H NMR (CDCl$_3$) δ=7.54 (m, 2H), 7.41 (m, 3H), 7.26 (s, 1H), 4.40 (m, 2H), 3.76 (m, 2H), 3.66 (m, 4H), 3.63 (m, 2H), 3.53 (m, 2H), 3.36 (s, 3H)

Example 1

1-[2-(2-(2-Methoxyethoxy)-ethoxy)-ethoxy-carbonyloxymethyl]-4-[N'-cyano-N"-(6-(4-chlorophenoxy)-hexyl)-N-guanidino]-pyridinium chloride A mixture of N-(6-(4-chlorophenoxy)-hexyl)-N'-cyano-N"-(4-pyridyl)-guanidine (1.13 g) and chloromethyl 2-(2-(2-methoxyethoxy)-ethoxy)-ethyl carbonate (1.95 g) was placed in a preheated oil bath at 100° C. After 15 minutes a clear orange melt was formed and after a further 45 minutes the mixture was cooled to room temperature and EtOAc (5 ml) was added. The desired compound crystallised and was isolated by filtration. Recrystallisation from isopropanol afforded an analytically pure sample.

$^{13}$C NMR (DMSO) δ=157.4, 155.0, 153.0, 144.9, 129.1, 123.9, 116.1, 115.0, 112.8, 80.2, 71.1, 69.6, 69.5, 68.0, 67.7, 67.6, 57.9, 42.2, 28.3, 25.7, 25.0

Example 2

1-[2-(2-Methoxyethoxy)-ethoxy-carbonyloxymethyl]-4-[N'-cyano-N"-(6-(4-chlorophenoxy)-hexyl)-N-guanidino]-pyridinium chloride By following the procedure described in Example 1 but substituting chloromethyl 2-(2-methoxyethoxy)-ethyl carbonate for chloromethyl 2-(2-(2-methoxyethoxy)-ethoxy)-ethyl carbonate, the title compound was isolated as a nicely crystalline compound.

$^{13}$C NMR (DMSO) δ=157.4, 155.0, 153.0, 144.9, 129.1, 123.9, 116.1, 115.0, 112.7, 80.2, 71.1, 69.4, 68.0, 67.7, 67.6, 58.0, 42.2, 28.3, 25.7, 25.0

Example 3

1-[2-Methoxyethoxy)-carbonyloxymethyl]4-[N'-cyano-N"-(6-(4-chlorophenoxy)-hexyl)-N-guanidino]-pyridinium chloride By following the procedure described in Example 1 but substituting chloromethyl 2-methoxyethyl carbonate for chloromethyl 2-(2-(2-methoxyethoxy)-ethoxy)-ethyl carbonate, the title compound was isolated as a crystalline compound.

$^{13}$C NMR (DMSO) δ=157.4, 155.0, 153.0, 144.8, 129.1, 123.9, 116.1, 115.0, 112.8, 80.2, 69.2, 67.8, 67.6, 57.9, 42.1, 28.3, 28.2, 25.7, 25.0

Example 4

1-[2-(2-(2-Methoxyethoxy)-ethoxy)-ethoxy-carbonyloxymethyl]-4-[N'-cyano-N"-(6-(4-chlorophenoxy)-hexyl)-N-guanidino]-pyridinium iodide Iodomethyl 2-(2-(2-methoxyethoxy)-ethoxy)-ethyl carbonate (10 g) was added to a hot solution of N-(6-(4-chlorophenoxy)-hexyl)-N'-cyano-N"-(4-pyridyl)-guanidine (6.4 g) in dry acetonitrile (240 ml) followed by reflux for 20 minutes. The mixture was then cooled to room temperature and the solvent removed in vacuo. The crystalline residue was stirred with ethyl acetate (100 ml) and isolated by filtration.

$^1$H NMR (DMSO) δ=10.2 (1H,br), 8.9 (1H,br), 8.7 (2H, d), 7.5 (2H,br), 7.31 (2H,d), 6.94 (2H,d), 6.23 (2H,s), 4.26 (2H,m), 3.96 (2H,t), 3.62 (2H,m), 3.55–3.3 (10H,m), 3.22 (3H,s), 1.71 (2H,m), 1.59 (2H,m), 1.40 (4H,m)

Example 5

N-[1-(2-(2-(2-Methoxyethoxy)-ethoxy)-ethoxycarbonyloxymethyl)-1,4-dihydropyridin-4-ylidene]-N'-cyano-N"-(6-(4-chlorophenoxy)-hexyl)-guanidine The compound of Example 4 was dissolved in dichloromethane, washed with an excess of aqueous sodium bicarbonate and sodium thiosulfate, dried over magnesium sulfate, filtered and evaporated in vacuo to leave the title compound as a yellow oil.

$^{13}$C NMR (DMSO) δ=157.4, 153.3, 129.1, 123.9, 116.1, 79.1, 71.2, 69.6, 69.5, 67.8, 67.7, 67.6, 61.6, 57.9, 28.4, 25.9, 25.4, 25.0

Example 6

1-[2-(2-(2-Methoxyethoxy)-ethoxy)-ethoxy-carbonyloxymethyl]-4-[N'-cyano-N"-(6-(4-chlorophenoxy)-hexyl)-N-guanidino]-1-pyridinium chloride The product of Example 5 was dissolved in dichloromethane and treated with an excess of HCl in ether. The solvents were evaporated in vacuo and the residue was redissolved in a small volume of dichloromethane. Addition of isopropanol followed by removal of dichloromethane in vacuo gave crystalline title compound identical with the product of Example 1.

Example 7

1-[1-(2-(2-Methoxyethoxy)-ethoxy-carbonyloxy)-ethyl]-4-[N'-cyano-N"-(6-(4-chlorophenoxy)-hexyl)-N-guanidino]-pyridinium chloride This compound was prepared by following the procedures described in Examples 4, 5 and 6 but substituting the mixture of 1-iodoethyl 2-(2-methoxyethoxy)-ethyl carbonate and the corresponding chloroethyl compound (Preparation 6) for iodomethyl 2-(2-(2-methoxyethoxy)-ethoxy)-ethyl carbonate.

$^1$H NMR (DMSO) δ=11.78 (br,1H), 9.03 (br,1H), 8.88 (d,2H), 7.66 (br,2H), 7.30 (d,2H), 6.94 (d,2H), 6.78 (q,1H), 4.22 (m,2H), 3.96 (t,2H), 3.70–3.40 (m,8H), 3.22 (s,3H), 1.83 (d,3H), 1.71 (m,2H), 1.59 (m,2H), 1.50–1.30 (m,4H)

Example 8

1-[2-(2-(2-Methoxyethoxy)-ethoxy)-ethoxy-acetoxymethyl]-4-[N'-cyano-N"-(6-(4-chlorophenoxy)-hexyl)-N-guanidino]-pyridinium chloride This compound was prepared by following the procedure described in Example 1 but substituting chloromethyl 2-(2-(2-methoxyethoxy)-ethoxy)-ethoxy-acetate for chloromethyl 2-(2-(2-methoxyethoxy)-ethoxy)-ethyl carbonate. The crystalline title compound was recrystallised from isopropanol.

$^{13}$C NMR (DMSO) δ=169.5, 157.4, 154.8, 144.9, 129.1, 123.9, 116.1, 115.0, 113.0, 77.6, 71.2, 70.1, 69.6, 69.6, 69.5, 67.6, 67.2, 57.9, 42.2, 28.3, 28.2, 25.7, 25.0

Example 9

1-[2-(2-(2-(2-Methoxyethoxy)-ethoxy)-ethoxy)-ethoxy-carbonyloxymethyl]-4-[N'-cyano-N"-(6-(4-chlorophenoxy)-hexyl)-N-guanidino]-pyridinium chloride The title compound was prepared as described in Examples 4, 5 and 6 but by substituting iodomethyl 2-(2-(2-(2-methoxyethoxy)-ethoxy)-ethoxy)-ethyl carbonate for iodomethyl 2-(2-(2-methoxyethoxy)-ethoxy)-ethyl carbonate in Example 4. Crystalline compound (from isopropanol).
$^{13}$C NMR (DMSO) δ=157.4, 155.0, 153.0, 144.8, 129.1, 123.9, 116.1, 80.2, 71.2, 69.7, 69.7, 69.6, 69.6, 69.5, 68.1, 67.7, 67.6, 57.9, 28.3, 25.7, 25.0

Example 10

1-Pivaloyloxymethyl-4-[N'-cyano-N"-(6-(4-chlorophenoxy)-hexyl)-N-guanidino]-pyridinium chloride A mixture of N-(6-(4-chlorophenoxy)-hexyl)-N'-cyano-N"-(4-pyridyl)-guanidine (0.5 g) and chloromethyl pivalate(1 ml) was placed in a preheated oil bath at 100° C. A clear yellow solution was formed after 10 minutes followed by spontaneous crystallisation a few minutes later. After a further 15 minutes at 100° C., the mixture was cooled to room temperature and treated with EtOAc. The crystalline product was isolated by filtration and recrystallised from isopropanol.
$^{13}$C NMR (DMSO) δ=176.5, 157.4, 154.8, 144.5, 129.1, 123.9, 116.1, 115.0, 77.8, 67.6, 38.2, 28.3, 26.3, 25.7, 25.0

Example 11

1-Acetoxymethyl-4-[N'-cyano-N"-(6-(4-chlorophenoxy)-hexyl)-N-guanidino]-pyridinium chloride The title compound was prepared as described in Example 10 but by substituting chloromethyl acetate for chloromethyl pivalate. The raw product was purified by chromatography on Sephadex LH-20 with dichloromethane/hexane/methanol (75:15:10) as eluent followed by crystallisation from isopropanol.
$^{13}$C NMR (DMSO) δ=169.6, 157.4, 154.8, 144.7, 129.1, 123.9, 116.1, 115.1, 112.8, 77.6, 67.6, 42.1, 28.4, 28.2, 25.7, 25.0, 20.3

Example 12

1-(L)-Valyloxymethyl-4-[N'-cyano-N"-(6-(4-chlorophenoxy)-hexyl)-N-guanidino]-pyridinium chloride, hydrochloride A mixture of N-(6-(4-chlorophenoxy)-hexyl)-N'-cyano-N"-(4-pyridyl)-guanidine (1.0 g) and N-tert-butoxycarbonyl-(L)-valine chloromethyl ester (3.4 g) was placed in a preheated oil bath at 90° C. for 70 minutes. After cooling to room temperature the reaction mixture was triturated with ether in order to remove unreacted chloromethyl ester. The remaining oil was taken up in dichloromethane and extracted with an excess of aqueous sodium bicarbonate. The organic phase was dried and evaporated in vacuo to leave an oil which was purified by chromatography on silica gel. The desired intermediate was dissolved in dichloromethane and treated at room temperature with an excess of hydrogen chloride in ether for 75 minutes. The crystalline product was isolated by filtration, washed with ether and dried in vacuo. Recrystallisation from methanol/ether afforded the analytically pure title compound.
$^{1}$H NMR (D$_2$O) δ=8.84 (2H,d), 7.7 (2H,br), 7.41 (2H,d), 7.05 (2H,d), 6.55 2H,dd), 4.34 (1H,d), 4.15 (2H,t), 3.62 (2H,t), 2.53 (1H,m), 2.0–1.7 (4H,m), 1.65–1.45 (4H,m), 1.13 (6H,t)

Example 13

1-Glycyloxymethyl-4-[N'-cyano-N"-(6-(4-chlorophenoxy)-hexyl)-N-guanidino]-pyridinium chloride hydrochloride The title compound was prepared as described in Example 12 but by substituting N-tert-butoxycarbonyl-glycine chhoromethyl ester for N-tert-butoxycarbonyl-(L)-valine chloromethyl ester. The title compound was isolated as an amorphous powder.
$^{13}$C NMR (DMSO) δ=166.9, 157.4, 145.0, 129.1, 123.9, 116.1, 78.1, 67.6, 28.3, 25.7, 25.0

Example 14

1-[Monobenzyl succinyloxymethyl]-4-[N'-cyano-N"-(6-(4-chlorophenoxy)-hexyl)-N-guanidino]-pyridinium chloride This compound was prepared as described in Example 1 but substituting chloromethyl benzyl succinate for chloromethyl 2-(2-(2-methoxy-ethoxy)-ethoxy)-ethyl carbonate. The title compound was isolated as a nice crystalline compound.
$^{13}$C NMR (DMSO) δ=171.5, 171.3, 157.4, 154.7, 144.7, 135.9, 129.1, 128.3, 127.9, 127.8, 123.9, 116.1, 114.8, 77.6, 67.6, 65.6, 28.3, 28.2, 25.7, 25.0

Example 15

1-[2-(2-(2-(2-(2-Methoxyethoxy)-ethoxy)-ethoxy)-ethoxy)-ethoxy carbonyloxymethyl]-4-[N'-cyano-N"-(6-(4-chlorophenoxy)-hexyl)-N-guanidino]-pyridinium chloride The title compound was prepared as described in Examples 4, 5 and 6 but substituting iodomethyl 2-(2-(2-(2-(2-methoxyethoxy)-ethoxy)-ethoxy)-ethoxy)-ethyl carbonate for iodomethyl 2-(2-(2-methoxyethoxy)-ethoxy)-ethyl carbonate in Example 4. Crystalline compound (from isopropanol).
$^{1}$H NMR (DMSO) δ=8.9 (Br, 1H), 8.7 (Br, 2H), 7.5 (Br, 2H), 7.30 (d, 2H), 6.94 (d, 2H), 6.20 (s, 2H), 4.25 (m, 2H), 3.95 (t, 2H), 3.62 (m, 2H), 3.50 (s, 16H), 3.43 (m, 2H), 3.23 (s, 3H), 1.71 (m, 2H), 1.58 (m, 2H), 1.40 (m, 4H)

Example 16

1-[2-(2-(2-(2-(2-(2-Methoxyethoxy)-ethoxy)-ethoxy)-ethoxy-ethoxy-ethoxy-carbonyloxymethyl]-4-[N'-cyano-N"-(6-(4-chlorophenoxy)-hexyl)-N-guanidino]-pyridinium chloride The title compound was prepared as described in Examples 4, 5 and 6 but substituting iodomethyl 2-(2-(2-(2-(2-(2-methoxyethoxy)-ethoxy)-ethoxy)-ethoxy)-ethoxy)- ethyl carbonate for iodomethyl 2-(2-(2-methoxyethoxy)-ethoxy)-ethyl carbonate in Example 4. Crystalline compound (from isopropanol).

$^1$H NMR (DMSO) δ=11.8 (Br, 1H), 9.0 (Br, 1H), 8.7 (Br, 2H), 7.5 (Br, 2H), 7.30 (d, 2H), 6.94 (d, 2H), 6.21 (s, 2H), 4.25 (m, 2H), 3.95 (t, 2H), 3.62 (m, 2H), 3.49 (s, 20H), 3.42 (m, 2H), 3.23 (s, 3H), 1.71 (m, 2H), 1.58 (m, 2H), 1.40 (m, 4H)

Example 17

1-[2-(2-(2-Methoxyethoxy)-ethoxy)-ethoxy-carbonyloxymethyl]-4-[N'-cyano-N"-(9-(diethoxyphosphinoyloxy)-nonyl)-N-guanidino]-pyridinium chloride Iodomethyl 2-(2-(2-methoxyethoxy)-ethoxy)-ethyl carbonate (3.2 g) was added to a hot solution of N-(9-(diethoxyphosphinoyloxy)-nonyl)-N'-cyano-N"-(4-pyridyl)-guanidine (2.5 g) in dry acetonitrile (85 ml) followed by reflux for 20 minutes. The mixture was then cooled to room temperature and the solvent removed in vacuo. The resulting oil was taken up in dichloromethane, washed with aqueous sodium bicarbonate and sodium thiosulfate, dried over magnesium sulfate, filtered and evaporated in vacuo to leave an oil which was dissolved in ethyl acetate. Water was added and the pH-value was lowered to 2 by the addition of aqueous hydrochloric acid to the stirred mixture. The aqueous phase was separated and freeze-dried. After addition of ethyl acetate, the crystalline title compound was isolated.

$^{13}$C NMR (DMSO) δ=155.2, 154.8, 153.0, 144.5, 115.3, 112.6, 80.1, 71.2, 69.6, 69.5, 68.0, 67.7, 66.8, 63.0, 57.9, 42.1, 29.6, 28.7, 28.4, 28.3, 26.0, 24.8, 15.9

Example 18

1-[2-(2-(2-Methoxyethoxy)-ethoxy)-ethoxy-carbonyloxymethyl]-4-[N'-cyano-N"-(12-(tert-butyloxycarbonylamino)-dodecyl)-N-guanidino]-pyridinium iodide The crystalline title compound was prepared as described in Example 4 but substituting N-(12-(tert-butyloxycarbonylamino)-dodecyl)-N'-cyano-N"-(4-pyridyl)-guanidine for N-(6-(4-chlorophenoxy)-hexyl)-N'-cyano-N"-(4-pyridyl)-guanidine.

$^1$H NMR (DMSO) δ=11.2 (Br, 1H), 8.88 (Br, 1H), 8.71 (d, 2H), 7.48 (Br, 2H), 6.72 (t, 1H), 6.22 (s, 2H), 4.26 (m, 2H), 3.63 (m, 2H), 3.6–3.3 (m, 8H), 3.21 (s, 3H), 2.87 (q, 2H), 1.55 (t, 2H), 1.37 (s, 9H), 1.4–1.15 (m, 20H)

Example 19

1-[2-(2-(2-Methoxyethoxy)-ethoxy)-ethoxy-carbonyloxymethyl]-4-[N'-cyano-N"-(12-(tert-butyloxycarbonylamino)-dodecyl)-N-guanidino]-pyridinium chloride The compound of Example 18 was suspended in ethyl acetate and washed with aqueous sodium bicarbonate and sodium thiosulfate followed by water. The organic phase was separated, water was added and aqueous hydrochloric acid was added with stirring to pH=2.2. The aqueous phase was separated and freeze-dried to leave a residue from which the title compound was isolated in crystalline form after the addition of ethyl acetate.

$^{13}$C NMR (DMSO) δ=155.6, 155.2, 153.1, 144.9, 115.1, 112.8, 80.3, 77.3, 71.3, 69.7, 69.6, 68.1, 67.8, 58.0, 42.4, 29.5, 29.0, 28.7, 28.6, 28.3, 26.3, 26.1

Example 20

1-[2-(2-(2-Methoxyethoxy)-ethoxy)-ethoxy-carbonyloxymethyl]-4-[N'-cyano-N"-(12-(tert-butyloxycarbonylamino)-dodecyl)-N-guanidino]-pyridinium chloride Prepared as described in Example 9 but substituting N-(12-(tert-butyloxycarbonylamino)-dodecyl)-N'-cyano-N"-(4-pyridyl)-guanidine for N-(6-(4-chlorophenoxy)-hexyl)-N'-cyano-N"-(4-pyridyl)-guanidine.

Example 21

1-[3-(N-tert-butoxycarbonylamino)-propyloxy-carbonyloxymethyl]-4-[N'-cyano-N"-(6-(4-chlorophenoxy)-hexyl)-N-guanidino]-pyridinium iodide Iodomethyl 3-(N-tert-butoxycarbonylamino)-propyl carbonate (2.5 g) was added to a hot solution of N-(6-(4-chlorophenoxy)-hexyl)-N'-cyano-N"-(4-pyridyl)-guanidine (1.7g) in dry acetonitrile (90 ml) followed by reflux for 20 minutes. The title compound crystallised on cooling to room temperature and was isolated by filtration.

$^1$H NMR (DMSO) δ=11.2 (Br, 1H), 8.9 (Br, 1H), 8.72 (d, 2H), 7.5 (Br, 2H), 7.30 (d, 2H), 6.94 (d, 2H), 6.85 (t, 1H), 6.21 (s, 2H), 4.14 (t, 2H), 3.96 (t, 2H), 3.33 (q, 2H), 2.97 (q, 2H), 1.75–1.35 (m, 10H), 1.36 (s, 9H)

Example 22

1-[3-Amino-propyloxy-carbonyloxymethyl]-4-[N'-cyano-N"-(6-(4-chlorophenoxy)-hexyl)-N-guanidino]-pyridinium chloride, hydrochloride A suspension of 1-[3-(N-tert-butoxycarbonylamino)-propyloxy-carbonyloxymethyl]-4-[N'-cyano-N"-(6-(4-chlorophenoxy)-hexyl)-N-guanidino]-pyridinium iodide (2.2 g) was shaken with an excess of sodium bicarbonate. The organic phase was dried over magnesium sulfate and filtered. The clear filtrate was cooled in ice with stirring and treated with an excess of hydrogen chloride in ether. The ice bath was removed and after stirring for 45 minutes, the solvent was removed in vacuo. Ethyl acetate was added and the crystalline material was isolated by filtration. Recrystallisation from ethanol gave the analytically pure title compound.

$^{13}$C NMR (DMSO) δ=157.4, 155.0, 152.8, 144.8, 129.1, 123.9, 116.1, 115.1, 112.8, 80.2, 67.6, 66.0, 35.6, 28.3, 25.9, 25.7, 25.0

Example 23

1-[3-(N-tert-butoxycarbonylamino)-propyl-carbamoyloxymethyl]-4-[N'-cyano-N"-(6-(4-chlorophenoxy)-hexyl)-N-guanidino]-pyridinium iodide Iodomethyl N-(3-(N-tert-butoxycarbonylamino)-propyl) carbamate (0.5 g) was added to a hot solution of N-(6-(4-chlorophenoxy)-hexyl)-N'-cyano-N"-(4-pyridyl)-guanidine (0.35 g) in dry acetonitrile (15 ml) followed by reflux for 20 minutes. After cooling to room temperature and evaporation in vacuo, the title compound crystallised from ethyl acetate and was isolated by filtration.

$^1$H NMR (DMSO) δ=11.2 (Br, 1H), 8.9 (Br, 1H), 8.68 (d, 2H), 7.73 (t, 1H), 7.5 (Br, 2H), 7.31 (d, 2H), 6.94 (d, 2H), 6.75 (t, 1H), 6.12 (s, 2H), 3.95 (t, 2H), 3.30 (q, 2H), 2.99 (q, 2H), 2.89 (q, 2H), 1.73–1.35 (m, 10H), 1.36 (s, 9H)

Example 24

1-[3-Aminopropyl-carbamoyloxymethyl]-4-[N'-cyano-N''-(6-(4-chlorophenoxy)-hexyl)-N-guanidino]-pyridinium chloride hydrochloride This compound was prepared as described in Example 22 but substituting 1-[3-(N-tert-butoxycarbonylamino)-propyl-carbamoyloxymethyl]-4-[N'-cyano-N''-(6-(4-chlorophenoxy)-hexyl)-N-guanidino]-pyridinium iodide for 1-[3-(N-tert-butoxycarbonylamino)-propyloxy-carbonyloxymethyl]-4-[N'-cyano-N''-(6-(4-chlorophenoxy)-hexyl)-N-guanidino]-pyridinium iodide. Isolated as a light yellow powder after crystallisation from isopropanol and recrystallisation from methanol/ether.

$^1$H NMR (DMSO) δ=11.9 (Br, 1H), 9.1 (Br, 1H), 8.71 (d, 2H), 8.03 (Br, 3H), 7.96 (t, 1H), 7.60 (Br, 2H), 7.30 (d, 2H), 6.95 (d, 2H), 6.13 (s, 2H), 3.95 (t, 2H), 3.36 (q, 2H), 3.06 (q, 2H), 2.75 (m, 2H), 1.69 (m, 4H), 1.58 (m, 2H), 1.40 (m, 4H)

Example 25

1-[5-(N-tert-butoxycarbonylamino)-pentanoyloxymethyl]-4-[N'-cyano-N''-(6-(4-chlorophenoxy)-hexyl)-N-guanidino]-pyridinium iodide Iodomethyl 5-(N-tert-butoxycarbonylamino)-pentanoate (1.5 g) was added to a hot solution of N-(6-(4-chlorophenoxy)-hexyl)-N'-cyano-N''-(4-pyridyl)-guanidine (1.04 g) in dry acetonitrile (45 ml) followed by reflux for 20 minutes. After cooling to room temperature and evaporation in vacuo, the title compound crystallised from ethyl acetate and was isolated by filtration as a light yellow powder.

$^1$H NMR (DMSO) δ=11.2 (Br, 1H), 8.9 (Br, 1H), 8.88 (d, 2H), 7.48 (Br, 2H), 7.30 (d, 2H), 6.95 (d, 2H), 6.76 (t, 1H), 6.18 (s, 2H), 3.95 (t, 2H), 3.30 (q, 2H), 2.88 (q, 2H), 2.41 (t, 2H), 1.75–1.35 (m, 12H), 1.36 (s, 9H)

Example 26

1-[5-Amino-2pentanoyloxymethyl]-4-[N'-cyano-N''-(6-(4-chlorophenoxy)-hexyl)-N-guanidino]-pyridinium chloride, hydrochloride This compound was prepared as described in Example 22 but substituting 1-[5-(N-tert-butoxycarbonylamino)-pentanoyloxymethyl]-4-[N'-cyano-N''-(6-(4-chlorophenoxy)-hexyl)-N-guanidino]-pyridinium iodide for 1-[3-(N-tert-butoxycarbonylamino)-propyloxy-carbonyloxymethyl]-4-[N'-cyano-N''-(6-(4-chlorophenoxy)-hexyl)-N-guanidino]-pyridinium iodide. Isolated as a colourless powder from ethyl acetate.

$^1$H NMR (DMSO) δ=12.0 (Br, 1H), 9.2 (Br, 1H), 8.78 (d, 2H), 8.07 (Br, 3H), 7.65 (Br, 2H), 7.30 (d, 2H), 6.95 (d, 2H), 6.22 (s, 2H), 3.96 (t, 2H), 3.41 (m, 2H), 2.74 (m, 2H), 2.44 (m, 2H), 1.71 (m, 2H), 1.58 (m, 6H), 1.40 (m, 4H)

Example 27

1-[3-(tert-butoxycarbonyl)-propionyloxymethyl]-4-[N'-cyano-N''-(6-(4-chlorophenoxy)-hexyl)-N-guanidino]-pyridinium chloride A mixture of N-(6-(4-chlorophenoxy)-hexyl)-N'-cyano-N''-(4-pyridyl)-guanidine (2.0 g) and chloromethyl tert-butyl succinate (3.01 g) was placed in a preheated oil bath at 90° C. After 20 minutes a clear melt was formed and after a further 20 minutes the mixture was cooled to room temperature and EtOAc (10 ml) was added. The desired compound crystallised and was isolated by filtration.

$^{13}$C NMR (DMSO) δ=171.4, 170.8, 157.4, 154.7, 144.8, 129.1, 123.9, 116.1, 115.0, 112.7, 80.1, 77.5, 67.6, 42.2, 29.4, 28.4, 28.3, 28.2, 27.6, 25.7, 25.0

Example 28

1-[3-carboxy-propionyloxymethyl]-4-[N'-cyano-N''-(6-(4-chlorophenoxy)-hexyl)-N-guanidino]-pyridinium chloride 5M Hydrochloric acid in diethyl ether (2.6 ml) was added with stirring to an ice-cold solution of 1-[3-(tert-butoxycarbonyl)-propionyloxymethyl]-4-[N'-cyano-N''-(6-(4-chlorophenoxy)-hexyl)-N-guanidino]-pyridinium chloride (0.78 g) in dichloromethane (35 ml). After stirring at room temperature for 3 hours the solvents were evaporated in vacuo; isopropanol was added and the title compound was isolated by filtration and recrystallised from isopropanol.

$^{13}$C NMR (DMSO) δ=173.1, 171.6, 157.4, 154.7, 144.8, 129.1, 123.9, 116.1, 115.0, 112.9, 77.5, 67.6, 42.2, 28.4, 28.4, 28.2, 25.7, 25.4, 25.0

Example 29

1-[N-(tert-butoxycarbonylmethyl)-carbamoyloxymethyl]-4-[N'-cyano-N''-(6-(4-chlorophenoxy)-hexyl)-N-guanidino]-pyridinium iodide Iodomethyl N-(tert-butoxycarbonylmethyl)-carbamate (2.84 g) was added to a hot solution of N-(6-(4-chlorophenoxy)-hexyl)-N'-cyano-N''-(4-pyridyl)-guanidine (2.23 g) in dry acetonitrile (100 ml) followed by reflux for 20 minutes. After cooling to room temperature and evaporation in vacuo, the title compound crystallised from ethyl acetate and was isolated by filtration as a light yellow powder.

$^1$H NMR (DMSO) δ=11.2 (Br, 1H), 8.9 (Br, 1H), 8.69 (d, 2H), 8.13 (t, 1H), 7.51 (Br, 2H), 7.31 (d, 2H), 6.94 (d, 2H), 6.16 (s, 2H), 3.96 (t, 2H), 3.66 (d, 2H), 3.3 (q, 2H), 1.71 (m, 2H), 1.58 (m, 2H), 1.48–1.34 (m, 4H), 1.38 (s, 9H)

Example 30

1-[N-(carboxymethyl)-carbamoyloxymethyl]-4-[N'-cyano-N''-(6-(4-chlorophenoxy)-hexyl)-N-guanidino]-pyridinium chloride A suspension of 1-[N-(tert-butoxycarbonylmethyl)-carbamoyloxymethyl]-4-[N'-cyano-N''-(6-(4-chlorophenoxy)-hexyl)-N-guanidino]-pyridinium iodide (2.0 g) in dichloromethane (60 ml) was shaken with an excess of sodium bicarbonate. The organic phase was dried over magnesium sulfate and filtered. The clear filtrate was cooled in ice with stirring and treated with 5M hydrogen chloride in ether (5.8 ml). The ice bath was removed and after stirring for 4 hours, the solvent was removed in vacuo. Isopropanol was added and the colourless crystalline material was isolated by filtration $^{13}$C NMR (DMSO) δ=170.7, 157.4, 154.7, 144.6, 129.1, 123.9, 116.1, 115.0, 112.8, 78.2, 67.6, 42.0, 28.3, 28.2, 25.7, 25.4, 25.0, 21.4

Example 31

1-[1-(tert-butoxycarbonyl)-4-piperidyloxy-carbonyloxymethyl]-4-[N'-cyano-N''-(6-(4-chlorophenoxy)-hexyl)-N-guanidino]-pyridinium iodide Iodomethyl 1-(tert-butoxycarbonyl)-4-piperidyl carbonate (3.0 g) was added to a hot solution of N-(6-(4- chlorophenoxy)-hexyl)-N'-cyano-N"-(4-pyridyl)-guanidine (1.93 g) in dry acetonitrile (80 ml) followed by reflux for 20 minutes. After cooling to room temperature and evaporation in vacuo, the title compound crystallised from ethyl acetate and was isolated by filtration as a light yellow powder.

$^1$H NMR (DMSO) δ=11.3 (Br, 1H), 8.92 (Br, 1H), 8.72 (d, 2H), 7.49 (Br, 2H), 7.30 (d, 2H), 6.95 (d, 2H), 6.22 (s, 2H), 4.80 (m, 1H), 3.96 (t, 2H), 3.52 (m, 2H), 3.35 (m, 2H), 3.19 (m, 2H), 1.83 (m, 2H), 1.71 (m, 2H), 1.63–1.43 (m, 8H), 1.39 (s, 9H)

Example 32

1-[4-Piperidyloxy-carbonyloxymethyl]-4-[N'-cyano-N"-(6-(4-chlorophenoxy)-hexyl)-N-guanidino]-pyridinium chloride, hydrochloride A suspension of 1-[1-(tert-butoxycarbonyl)-4-piperidyloxy-carbonyloxy-methyl]-4-[N'-cyano-N"-(6-(4-chlorophenoxy)-hexyl)-N-guanidino]-pyridinium iodide (1.0 g) in dichloromethane (30 ml) was shaken with an excess of sodium bicarbonate. The organic phase was dried over magnesium sulfate and filtered. The clear filtrate was cooled in ice with stirring and treated with an excess of hydrogen chloride in ether. The ice bath was removed and after stirring for 4 hours, the solvent was removed in vacuo. The residue was crystallised from ethanol to afford the analytically pure title compound.

$^1$H NMR (DMSO) δ=11.9 (Br, 1H), 9.22 (Br, 3H), 8.73 (d, 2H), 7.58 (Br, 2H), 7.30 (d, 2H), 6.95 (d, 2H), 6.22 (s, 2H), 4.88 (m, 1H), 3.96 (t, 2H), 3.44 (Br, 2H), 3.09 (m, 4H), 2.07 (m, 2H), 1.89 (m, 2H), 1.71 (m, 2H), 1.58 (m, 2H), 1.41 (m, 4H)

Example 33

1-[tert-butoxycarbonylmethoxy-carbonyloxymethyl]-4-[N'-cyano-N"-(6-(4-chlorophenoxy)-hexyl)-N-guanidino]-pyridinium iodide Iodomethyl tert-butoxycarbonylmethyl carbonate (6.9 g) was added to a hot solution of N-(6-(4-chlorophenoxy)-hexyl)-N'-cyano-N"-(4-pyridyl)-guanidine (5.42 g) in dry acetonitrile (240 ml) followed by reflux for 20 minutes. After cooling to room temperature and evaporation in vacuo, the title compound crystallised from ethyl acetate and was isolated by filtration as a light yellow powder.

$^1$H NMR (DMSO) δ=11.2 (bs, 1H), 8.94 (bs, 1H), 8.74 (d, 2H), 7.51 (bs, 2H), 7.31 (d, 2H), 6.95 (d, 2H), 6.29 (s, 2H), 4.67 (s, 2H), 3.96 (t, 2H), 3.29 (m, 2H), 1.69 (m, 2H), 1.58 (m, 2H), 1.43 (m, 4H), 1.43 (s, 9H)

Example 34

1-[Carboxymethoxy-carbonyloxymethyl]-4-[N'-cyano-N"-(6-(4-chlorophenoxy)-hexyl)-N-guanidino]-pyridinium chloride Prepared as described in Example 30 but substituting 1-[tert-butoxy-carbonylmethoxy-carbonyloxymethyl]-4-[N'-cyano-N"-(6-(4-chlorophenoxy)-hexyl)-N-guanidino]-pyridinium iodide for 1-[N-(tert-butoxy-carbonylmethyl)-carbamoyloxymethyl]-4-[N'-cyano-N"-(6-(4-chlorophenoxy)-hexyl)-N-guanidino]-pyridinium iodide.

$^1$H NMR (DMSO) δ=13.2 (bs, 1H), 11.9 (bs, 1H), 9.56 (bs, 2H), 8.72 (d, 2H), 7.70 (bs, 2H), 7.30 (d, 2H), 6.94 (d, 2H), 6.27 (s, 2H), 4.68 (s, 2H) 3.96 (t, 2H), 3.38 (bm, 2H), 1.69 (bm, 2H), 1.59 (m, 2H), 1.41 (bm, 4H)

Example 35

N-[1-(α-(2-(2-(2-Methoxyethoxy)-ethoxy)-ethoxycarbonyloxy)benzyl)-1,4-dihydropyridin-4-ylidene]-N'-cyano-N"-(6-(4-chlorophenoxy)-hexyl)-guanidine A mixture of N-(6-(4-chlorophenoxy)-hexyl)-N'-cyano-N"-(4-pyridyl)-guanidine (67 mg) and α-chlorobenzyl 2-(2-(2-methoxyethoxy)-ethoxy)-ethyl carbonate (150 mg) was placed in a preheated oil bath at 90° C. After 10 minutes a clear yellow melt was formed and after a further 20 minutes the mixture was cooled to room temperature and EtOAc (4 ml) was added. Decantation and evaporation in vacuo gave a residue which was treated with ether. After decantation of the ether, the residue was taken up in dichloromethane and washed with an excess of sodium bicarbonate. Chromatography on silica gel with dichloromethane/methanol (98:2) as eluent gave the title compound as a colourless oil.

$^1$H NMR (DMSO) δ=7.70 (d, 2H), 7.48 (m, 5H), 7.42 (s, 1H), 7.30 (d, 2H), 6.92 (d, 2H), 6.13 (d, 2H), 4.32 (m, 2H), 3.95 (t, 2H), 3.65 (t, 2H), 3.52 (m, 6H), 3.42 (m, 2H), 3.22 (s, 3H), 3.10 (m, 2H), 1.2–1.8 (m, 8H)

Example 36

Solubility in Water of Compounds of Formula I

The solubility in water of compounds of the present invention was determined by shaking the compounds in water for one hour at room temperature followed by filtration and determination of the concentration of the compound in the filtrate by HPLC. The solubility of the compounds prepared in Examples 8 and 9 was compared with the solubility of the parent compound, N-(6-(4-chlorophenoxy)-hexyl)-N'-cyano-N"-(4-pyridyl)-guanidine. The results appear from Table 1 below.

TABLE 1

| Compound | Solubility in water (mg/ml) |
| --- | --- |
| N-(6-(4-chlorophenoxy)-hexyl)-N'-cyano-N"-(4-pyridyl)-guanidine | 0.0002 |
| Compound of Example 8 | >50 |
| Compound of Example 9 | >50 |

The data in Table 1 clearly show that a significant increase in solubility is achieved by using the prodrugs of the present invention. The active compound is for all practical purposes insoluble, whereas the prodrug is soluble at more than 50 mg/g, which allow for the preparation of medicaments.

What is claimed is:

1. A compound of the formula I:

[I]

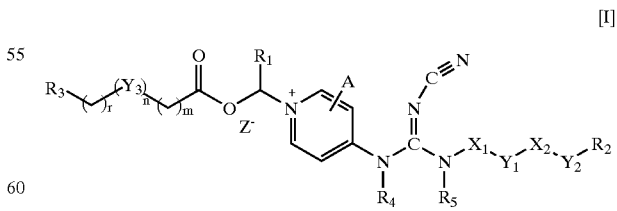

wherein $X_1$ and $X_2$ independently represent a bond; a straight, branched and/or cyclic hydrocarbon diradical, all of which are optionally substituted with one or more hydroxy, halogen, nitro, amino, cyano, aminosulfonyl, alkylsulfonylamino, alkylcarbonyl, formyl, aminocarbonyl or alkylcarbonylamino; a heteroarylene or non-aromatic heterocyclic hydrocarbon diradical, all of which are optionally substituted with one or more straight, branched and/or cyclic non-aromatic hydrocarbon radical, hydroxyl, halogen, amino, nitro, cyano, aminosulfonyl, alkylsulfonylamino, alkylcarbonyl, formyl, aminocarbonyl or alkylcarbonylamino;

$Y_1$ and $Y_2$ independently represent a bond, an ether diradical (R'—O—R"), an amine diradical (R'—N—R"), O, S, S(O), S(O)$_2$, C(O), NH—CO, CO—NH, SO$_2$—N(R'), methylene or N(R')—SO$_2$ wherein R' and R" independently represent straight or branched hydrocarbon diradicals containing up to 4 carbon atoms;

$Y_3$ represents O, O—C(O), C(O)—O, N(R$_8$), wherein R$_8$ is hydrogen or C$_{1-4}$alkyl;

$R_1$ represents hydrogen or straight, branched and/or cyclic alkyl, optionally substituted with phenyl; or an aromatic hydrocarbon radical;

$R_2$ represents aryl, heteroaryl or a non-aromatic heterocyclic hydrocarbon radical, all of which are optionally substituted, tetrahydropyranyloxy, di-(C$_{1-4}$ alkoxy) phosphinoyloxy and C$_{1-4}$ alkoxycarbonylamino;

$R_3$ represents hydrogen; a straight, branched and/or cyclic hydrocarbon radical, optionally substituted with one or more amino, hydroxy, carboxy, halogen, nitro, cyano, alkoxy, aminocarbonyl, C$_{1-4}$alkoxycarbonyl, C$_{1-4}$alkoxycarbonylamino, sulfo, hydroxysulfonyloxy, dihydroxyphosphinoyloxy, phosphono, sulfamino, aminosulfonyl, aminoacylamino or dialkoxyphosphinoyl; heteroaryl or a non-aromatic heterocyclic hydrocarbon radical, all of which are optionally substituted with one or more straight, branched and/or cyclic hydrocarbon radical, amino, hydroxy, carboxy, halogen, nitro, cyano, alkoxy, aminocarbonyl, C$_{1-4}$alkoxycarbonyl, C$_{1-4}$alkoxycarbonylamino, sulfo, hydroxysulfonyloxy, dihydroxyphosphinoyloxy, phosphono, sulfamino, aminosulfonyl, aminoacylamino or dialkoxyphosphinoyl; or the formula:

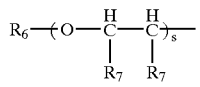

wherein s is an integer from 1 to 200; R$_6$ is hydrogen or an optionally substituted non-aromatic hydrocarbon radical; R$_7$ is independently hydrogen or methyl;

$R_4$ and $R_5$ independently represent hydrogen; a straight, branched and/or cyclic hydrocarbon radical, optionally substituted with halogen, hydroxyl, halogen, amino, nitro or cyano;

A represents hydrogen, an optionally substituted, straight, branched and/or cyclic hydrocarbon radical, hydroxy, halogen, nitro, cyano, heteroaryl, heteroaralkyl or thiol;

Z$^-$ is a pharmaceutically acceptable anion;

m and r are independently an integer from 0 to 4; and n is 0 or 1.

2. A compound of the general formula II:

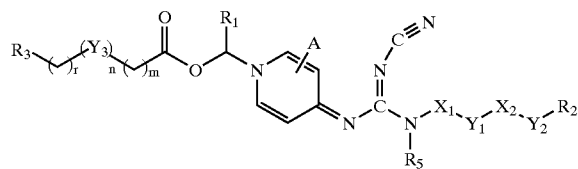

wherein $X_1$ and $X_2$ independently represent a bond; a straight, branched and/or cyclic hydrocarbon diradical, all of which are optionally substituted with one or more hydroxy, halogen, nitro, amino, cyano, aminosulfonyl, alkylsulfonylamino, alkylcarbonyl, formyl, aminocarbonyl or alkylcarbonylamino; a heteroarylene or non-aromatic heterocyclic hydrocarbon diradical, all of which are optionally substituted with one or more straight, branched and/or cyclic non-aromatic hydrocarbon radical, hydroxyl, halogen, amino, nitro, cyano, aminosulfonyl, alkylsulfonylamino, alkylcarbonyl, formyl, aminocarbonyl or alkylcarbonylamino;

$Y_1$ and $Y_2$ independently represent a bond, an ether diradical (R'—O—R"), an amine diradical (R'—N—R"), O, S, S(O), S(O)$_2$, C(O), NH—CO, CO—NH, SO$_2$—N(R'), methylene or N(R')—SO$_2$ wherein R' and R" independently represent straight or branched hydrocarbon diradicals containing up to 4 carbon atoms;

$Y_3$ represents O, O—C(O), C(O)—O, N(R$_8$), wherein R$_8$ is hydrogen or C$_{1-4}$alkyl;

$R_1$ represents hydrogen or straight, branched and/or cyclic alkyl, optionally substituted with phenyl; or an aromatic hydrocarbon radical;

$R_2$ represents aryl, heteroaryl or a non-aromatic heterocyclic hydrocarbon radical, all of which are optionally substituted, tetrahydropyranyloxy, di-(C$_{1-4}$ alkoxy) phosphinoyloxy and C$_{1-4}$ alkoxycarbonylamino;

$R_3$ represents hydrogen; a straight, branched and/or cyclic hydrocarbon radical, optionally substituted with one or more amino, hydroxy, carboxy, halogen, nitro, cyano, alkoxy, aminocarbonyl, C$_{1-4}$alkoxycarbonyl, C$_{1-4}$alkoxycarbonylamino, sulfo, hydroxysulfonyloxy, dihydroxyphosphinoyloxy, phosphono, sulfamino, aminosulfonyl, aminoacylamino or dialkoxyphosphinoyl; heteroaryl or a non-aromatic heterocyclic hydrocarbon radical, all of which are optionally substituted with one or more straight, branched and/or cyclic hydrocarbon radical, amino, hydroxy, carboxy, halogen, nitro, cyano, alkoxy, aminocarbonyl, C$_{1-4}$alkoxycarbonyl, C$_{1-4}$alkoxycarbonylamino, sulfo, hydroxysulfonyloxy, dihydroxyphosphinoyloxy, phosphono, sulfamino, aminosulfonyl, aminoacylamino or dialkoxyphosphinoyl; or the formula:

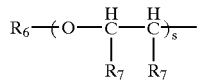

wherein s is an integer from 1 to 200; R$_6$ is hydrogen or an optionally substituted non-aromatic hydrocarbon radical; R$_7$ is independently hydrogen or methyl;

$R_5$ represents hydrogen; a straight, branched and/or cyclic hydrocarbon radical, optionally substituted with halogen, hydroxyl, halogen, amino, nitro or cyano;

A represents hydrogen, an optionally substituted, straight, branched and/or cyclic hydrocarbon radical, hydroxy, halogen, nitro, cyano, heteroaryl, heteroaralkyl or thiol;

m and r are independently an integer from 0 to 4; and n is 0 or 1.

3. The compound according to claim 1 or 2, wherein $X_1$ and $Y_1$ are both bonds;

$X_2$ is a straight, branched or cyclic, saturated or unsaturated $C_{4-20}$hydrocarbon diradical;

$Y_2$ is O, S, CO or methylene;

$R_1$ is hydrogen, straight or branched $C_{1-4}$alkyl, aralkyl or aryl;

$R_2$ is optionally substituted aryl, heteroaryl, di-($C_{1-4}$alkoxy)phosphinoyloxy, $C_{1-4}$alkoxycarbonylamino or tetrahydropyranyloxy;

$R_3$ is hydrogen, straight or branched $C_{1-6}$alkyl, $C_{3-6}$cycloalkyl, $C_{2-6}$alkenyl or $C_{2-6}$alkynyl, all of which are optionally substituted with amino, carboxy, aminocarbonyl or $C_{1-4}$alkoxycarbonyl; optionally substituted aryl, aralkyl, heteroaryl or $$R_6-(O-\underset{R_7}{\overset{H}{\underset{|}{C}}}-\underset{R_7}{\overset{H}{\underset{|}{C}}})_s-$$

wherein s is an integer from 1 to 200; $R_6$ is hydrogen or $C_{1-4}$alkyl;

each $R_7$ is independently hydrogen or methyl;

$Y_3$ is O or N($R_8$), wherein $R_8$ is hydrogen or $C_{1-4}$alkyl;

m and n are independently 0 or 1; and r is 0.

4. The compound according to claim 1 or 2, wherein n is 0, m is 0, and $R_3$ is straight or branched $C_{1-6}$alkyl optionally substituted with amino, hydroxy, carboxy, halogen, nitro, cyano, alkoxy, aminocarbonyl, $C_{1-4}$alkoxycarbonyl, $C_{1-4}$alkoxycarbonylamino, sulfo, hydroxysulfonyloxy, dihydroxyphosphinoyloxy, phosphono, sulfamino, aminosulfonyl, aminoacylamino or dialkoxyphosphinoyl.

5. The compound according to claim 1 or 2, wherein n is 1, m is 0, $Y_3$ is $NR_8$, wherein $R_8$ is hydrogen or $C_{1-4}$alkyl, and $R_3$ is hydrogen, straight or branched $C_{1-6}$alkyl optionally substituted with amino, hydroxy, carboxy, halogen, nitro, cyano, alkoxy, aminocarbonyl, $C_{1-4}$alkoxycarbonyl, $C_{1-4}$alkoxycarbonylamino, sulfo, hydroxysulfonyloxy, dihydroxyphosphinoyloxy, phosphono, sulfamino, aminosulfonyl, aminoacylamino or dialkoxyphosphinoyl; or $R_8$ and $R_3$ together with the nitrogen atom of $Y_3$ form a 5, 6 or 7-membered ring.

6. The compound according to claim 1 or 2, wherein n is 1, m is 0, $Y_3$ is O, and $R_3$ is straight or branched $C_{1-6}$ alkyl optionally substituted by amino, hydroxy, carboxy, halogen, nitro, cyano, alkoxy, aminocarbonyl, $C_{1-4}$alkoxycarbonyl, $C_{1-4}$alkoxycarbonylamino, sulfo, hydroxysulfonyloxy, dihydroxyphosphinoyloxy, phosphono, sulfamino, aminosulfonyl, aminoacylamino or dialkoxyphosphinoyl.

7. The compound according to claim 1 or 2, wherein n is 1, m is 0 or 1, $Y_3$ is O, and $R_3$ is $R_6$—(O—CH$_2$—CH$_2$)$_s$—, wherein s is an integer of from 1 to 150, and $R_6$ is hydrogen, methyl or ethyl.

8. The compound according to claim 7, wherein s is an integer from 2 to 10 and $R_6$ is methyl.

9. The compound according to claim 1 or 2, wherein n is 1, m is 0, $Y_3$ is O, and $R_3$ is a 5, 6 or 7 membered non-aromatic heterocyclic hydrocarbon.

10. The compound according to claim 9, wherein $R_3$ is pyrrolidinyl, piperidyl or hexahydro-1H-azepinyl.

11. The compound according to claim 1 or 2, wherein $R_2$ is optionally substituted aryl.

12. The compound according to claim 11, wherein $R_2$ is phenyl optionally substituted by one or more substituents selected from the group consisting of halogen, trifluoromethyl, hydroxy, $C_{1-4}$ alkyl, $C_{1-4}$ alkoxy, $C_{1-4}$alkoxycarbonyl, nitro, cyano, amino, aminocarbonyl, sulfamoyl or $C_{1-4}$hydroxyalkyl.

13. The compound according to claim 12, wherein said substituent is halogen.

14. The compound according to claim 1 or 2, wherein $Y_1$ is a bond, and $Y_2$ is O.

15. The compound according to claim 1 or 2, wherein $X_1$ is a bond, and $X_2$ is a $C_{4-12}$ hydrocarbon diradical.

16. The compound according to claim 1, said compound is selected from the group consisting of 1-[2-(2-(2-Methoxyethoxy)-ethoxy)-ethoxy-carbonyloxymethyl]-4-[N'-cyano-n"-(6-(4-chlorophenoxy)-hexyl)-N-guanidino]-pyridinium chloride; 1-[2-(2-Methoxyethoxy)-ethoxy-carbonyloxymethyl]-4-[N'-cyano-N"-(6-(4-chlorophenoxy)-hexyl)-N-guanidino]-pyridinium chloride; 1-[2-Methoxyethoxy)-carbonyloxymethyl]-4-[N'-cyano-N"-(6-(4-chlorophenoxy)-hexyl)-N-guanidino]-pyridinium chloride; 1-[2-(2-(2-Methoxyethoxy)-ethoxy)-ethoxy-carbonyloxymethyl]-4-[N'-cyano-N"-(6-(4-chlorophenoxy)-hexyl)-N-guanidino]-pyridinium iodide; N-[1-(2-(2-(2-Methoxyethoxy)-ethoxy)-ethoxycarbonyloxymethyl)-1,4-dihydropyridin-4-ylidene]-N'-cyano-N"-(6-(4-chlorophenoxy)-hexyl)-guanidine; 1-[2-(2-(2-Methoxyethoxy)-ethoxy)-ethoxy-carbonyloxymethyl]-4-[N'-cyano-N"-(6-(4-chlorophenoxy)-hexyl)-N-guanidino]-pyridinium chloride; 1-[1-(2-(2-Methoxyethoxy)-ethoxy-carbonyloxy)-ethyl]-4-[N'-cyano-N"-(6-(4-chlorophenoxy)-hexyl)-N-guanidino]-pyridinium chloride-[2-(2-(2-Methoxyethoxy)-ethoxy)-ethoxy-acetoxymethyl]-4-[N'-cyano-N"-(6-(4-chlorophenoxy)-hexyl)-N-guanidino]-pyridinium chloride; 1-[2-(2-(2-(2-Methoxyethoxy)-ethoxy)-ethoxy)-ethoxy-carbonyloxymethyl]-4-[N'-cyano-N"-(6-(4-chlorophenoxy)-hexyl)-N-guanidino]-pyridinium chloride; 1-Pivaloyloxymethyl-4-[N'-cyano-N"-(6-(4-chlorophenoxy)-hexyl)-N-guanidino]-pyridinium chloride; 1-Acetoxymethyl-4-[N'-cyano-N"-(6-(4-chlorophenoxy)-hexyl)-N-guanidino]-pyridinium chloride; 1-(L)-Valyloxymethyl-4-[N'-cyano-N"-(6-(4-chlorophenoxy)-hexyl)-N-guanidino]-pyridinium chloride, hydrochloride; 1-Glycyloxymethyl-4-[N'-cyano-N"-(6-(4-chlorophenoxy)-hexyl)-N-guanidino]-pyridinium chloride, hydrochloride; 1-[Monobenzyl succinyloxymethyl]-4-[N'-cyano-N"-(6-(4-chlorophenoxy)-hexyl)-N-guanidino]-pyridinium chloride; 1-[2-(2-(2-(2-Methoxyethoxy)-ethoxy)-ethoxy)-ethoxy carbonyloxymethyl]-4-[N'-cyano-N"-(6-(4-chlorophenoxy)-hexyl)-N-guanidino]-pyridinium chloride; 1-[2-(2-(2-(2-(2-Methoxyethoxy)-ethoxy)-ethoxy)-ethoxy-ethoxy-carbonyloxymethyl]-4-[N'-cyano-N"-(6-(4-chlorophenoxy)-hexyl)-N-guanidino]-pyridinium chloride; 1-[2-(2-(2-Methoxyethoxy)-ethoxy)-ethoxy-carbonyloxymethyl]-4-[N'-cyano-N"-(9-(diethoxyphosphinoyloxy)-nonyl)-N-guanidino]-pyridinium chloride; 1-[2-(2-(2-Methoxyethoxy)- ethoxy)-ethoxy)-carbonyloxymethyl]-4-[N'-cyano-N"-(12-(tert-butyloxycarbonylamino)-dodecyl)-N-guanidino]-pyridinium iodide; 1-[2-(2-(2-Methoxyethoxy)-ethoxy)-ethoxy)-carbonyloxymethyl]-4-[N'-cyano-N"-(12-(tert-butyloxycarbonylamino)-dodecyl)-N-guanidino]-pyridinium chloride; 1-[2-(2-(2-(2-Methoxyethoxy)-ethoxy)-ethoxy)-ethoxy-carbonyloxymethyl]-4-[N'-cyano-N"-(12-(tert-butyloxycarbonylamino)-dodecyl)-N-guanidino]-pyridinium chloride; 1-[3-(N-tert-butoxycarbonylamino)-propyloxy-carbonyloxymethyl]-4-[N'-cyano-N"-(6-(4-chlorophenoxy)-hexyl)-N-guanidino]-pyridinium iodide; 1-[3-Amino-propyloxy-carbonyloxymethyl]-4-[N'-cyano-N"-(6-(4-chlorophenoxy)-hexyl)-N-guanidino]-pyridinium chloride, hydrochloride; 1-[3-(N-tert-butoxycarbonylamino)-propyl-carbamoyloxymethyl]-4-[N'-cyano-N"-(6-(4-chlorophenoxy)-hexyl)-N-guanidino]-pyridinium iodide; 1-[3-Aminopropyl-carbamoyloxymethyl]-4-[N'-cyano-N"-(6-(4-chlorophenoxy)-hexyl)-N-guanidino]-pyridinium chloride, hydrochloride; 1-[5-(N-tert-butoxycarbonylamino)-pentanoyloxymethyl]-4-[N'-cyano-N"-(6-(4-chlorophenoxy)-hexyl)-N-guanidino]-pyridinium iodide; 1-[5-Amino-pentanoyloxymethyl]-4-[N'-cyano-N"-(6-(4-chlorophenoxy)-hexyl)-N-guanidino]-pyridinium chloride, hydrochloride; 1-[3-(tert-butoxycarbonyl)-propionyloxymethyl]-4-[N'-cyano-N"-(6-(4-chlorophenoxy)-hexyl)-N-guanidino]-pyridinium chloride; 1-[3-carboxy-propionyloxymethyl]-4-[N'-cyano-N"-(6-(4-chlorophenoxy)-hexyl)-N-guanidino]-pyridinium chloride; 1-[N-(tert-butoxycarbonylmethyl)-carbamoyloxymethyl]-4-[N'-cyano-N"-(6-(4-chlorophenoxy)-hexyl)-N-guanidino]-pyridinium iodide; 1-[N-(carboxymethyl)-carbamoyloxymethyl]-4-[N'-cyano-N"-(6-(4-chlorophenoxy)-hexyl)-N-guanidino]-pyridinium chloride; 1-[1-(tert-butoxycarbonyl)-4-piperidyloxy-carbonyloxymethyl]-4-[N'-cyano-N"-(6-(4-chlorophenoxy)-hexyl)-N-guanidino]-pyridinium iodide; 1-[4-Piperidyloxy-carbonyloxymethyl]-4-[N'-cyano-N"-(6-(4-chloro-phenoxy)-hexyl)-N-guanidino]-pyridinium chloride, hydrochloride; 1-[tert-butoxycarbonylmethoxy-carbonyloxymethyl]-4-[N'-cyano-N"-(6-(4-chlorophenoxy)-hexyl)-N-guanidino]-pyridinium iodide; 1-[Carboxymethoxy-carbonyloxymethyl]-4-[N'-cyano-N"-(6-(4-chlorophenoxy)-hexyl)-N-guanidino]-pyridinium chloride; N-[1-(α-(2-(2-(2-Methoxyethoxy)-ethoxy)-ethoxycarbonyloxy)benzyl)-1,4-dihydropyridin-4-ylidene]-N'-cyano-N"-(6-(4-chlorophenoxy)-hexyl)-guanidine.

17. A pharmaceutical composition comprising:
the compound of claim 1 or 2; and
a pharmaceutically acceptable excipient or diluent;
optionally together with one or more other anti-neoplastic compound.

18. A pharmaceutical composition in separate containers and intended for sequential or simultaneous administration, the compound of claim 1 or 2, and another anti-neoplastic compound, optionally together with pharmaceutically acceptable excipients or diluents.

19. The composition according to claim 17, wherein said compound(s) is present in unit dosage.

20. The composition according to claim 17, wherein the compound(s) is dissolved in an appropriate, pharmaceutically acceptable solvent.

21. The composition according to claim 17 for parenteral administration.

22. The composition according to claim 17, wherein said other antineoplastic compound(s) is selected from the list consisting of S-triazin derivatives, antibiotic agents, alkylating agents, anti-metabolites, anti-mitotic agents, hormonal agents, biological response modifiers and angiogenesis inhibitors.

23. The composition according to claim 17, wherein the compound of formula I or II is 1-[2-(2-(2-(2-methoxyethoxy)-ethoxy)-ethoxy)-ethoxy-carbonyloxymethyl]-4-[N'-cyano-N"-(6-(4-chlorophenoxy)-hexyl)-N-guanidino]-pyridinium chloride, and wherein the other anti-neoplastic agent(s) is selected from the group consisting of paclitaxel, fluorouacil, etoposide, cyclophosphamide, cisplatin, carboplatin, vincristine, gemcitabine, vinorelbine, chlorambucil, doxorubicin and melphalan.

24. The method of treating or ameliorating a proliferative disease or condition, the method comprising:
administering, to a patient in need thereof, a pharmaceutical composition comprising an effective amount of a compound of formula I or II according to claim 1 or 2, and
optionally simultaneously or sequentially therewith administering one or more other anti-neoplastic compound and/or ionising radiation.

25. The method according to claim 24, wherein said proliferative disease or condition is cancer.

26. The method according to claim 24, wherein said cancer is selected from the group consisting of leukaemia, acute myeloide leukaemia, chronic myeloide leukaemia, chronic lymphatic leukaemia, myelodysplasia, multiple myeloma, Hodgkin's disease or non-Hodgkin's lymphoma, small or non-small cell lung carcinoma, gastric, intestinal or colorectal cancer, prostate, ovarian or breast cancer, head, brain or neck cancer, cancer in the urinary tract, kidney or bladder cancer, malignant melanoma, lever cancer, uterine cancer and pancreatic cancer.

27. The method according to claim 24, wherein said other anti-neoplastic compound is selected from the group consisting of S-triazin derivatives, antibiotic agents, alkylating agents, anti-metabolites, anti-mitotic agents, hormonal agents, biological response modifiers and angiogenesis inhibitors.

28. The method according to claim 24, wherein the compound of formula I or II is 1-[2-(2-(2-(2-methoxyethoxy)-ethoxy)-ethoxy)-ethoxy-carbonyloxymethyl]-4-[N'-cyano-N"-(6-(4-chlorophenoxy)-hexyl)-N-guanidino]-pyridinium chloride, and wherein the other anti-neoplastic compound is selected from the group consisting of paclitaxel, fluorouacil, etoposide, cyclophosphamide, cisplatin, carboplatin, vincristine, gemcitabine, vinorelbine, chlorambucil, doxorubicin and melphalan.

29. The method according to claim 24, wherein said composition is parenterally administered.

30. The compound of claim 1, wherein said Z⁻ is selected from the group consisting of chloride, bromide, iodide, sulfate, methanesulfonate, p-toluenesulfonate, nitrate and phosphate.

31. The composition of claim 20, wherein said pharmaceutically acceptable solvent is selected from the group consisting of water, isotonic saline, isotonic glucose solution and a buffer solution.

32. The method of claim 29, wherein said composition is intravenously administered.

* * * * *